(12) United States Patent
Marban

(10) Patent No.: US 6,569,862 B1
(45) Date of Patent: May 27, 2003

(54) METHODS FOR TREATMENT OF DISORDERS OF CARDIAC CONTRACTILITY

(75) Inventor: Eduardo Marban, Lutherville, MD (US)

(73) Assignee: Johns Hopkins University, Baltimore, MD (US)

( * ) Notice: Subject to any disclaimer, the term of this patent is extended or adjusted under 35 U.S.C. 154(b) by 0 days.

(21) Appl. No.: 09/680,876

(22) Filed: Oct. 6, 2000

Related U.S. Application Data

(62) Division of application No. 09/186,755, filed on Nov. 5, 1998, now Pat. No. 6,191,136.
(60) Provisional application No. 60/064,942, filed on Nov. 7, 1997.

(51) Int. Cl.[7] ...................... A61K 31/505; A61K 31/54; A61K 31/53; A61K 31/445; A61K 31/425
(52) U.S. Cl. ................... 514/258; 514/222.2; 514/241; 514/315; 514/372; 514/401; 514/412
(58) Field of Search ............................. 514/258, 222.2, 514/241, 315, 372, 401, 412

(56) References Cited

U.S. PATENT DOCUMENTS

| | | | |
|---|---|---|---|
| 2,868,803 A | 1/1959 | Druey et al. ................. 260/310 |
| 3,474,098 A | 10/1969 | Hitchings et al. ......... 260/256.5 |
| 3,624,205 A | 11/1971 | Hitchings et al. ............ 424/251 |
| 3,682,957 A | 8/1972 | Cresswell et al. .......... 260/310 |
| 3,825,542 A | 7/1974 | Novello ................... 260/256 R |
| 3,864,341 A | 2/1975 | Cresswell et al. .... 260/247.2 A |
| 3,869,501 A | 3/1975 | Waddan ................... 260/465.3 |
| 3,890,313 A | 6/1975 | Novello ................... 260/243 D |
| 3,892,738 A | 7/1975 | Novello ................... 260/243 D |
| 3,892,858 A | 7/1975 | Novello ....................... 424/246 |
| 3,907,799 A | 9/1975 | O'Brien et al. ........... 260/256.4 |
| 3,920,652 A | 11/1975 | Springer et al. ......... 260/256.4 |
| 3,951,966 A | 4/1976 | Novello ................... 260/243 D |
| 3,951,967 A | 4/1976 | Novello ................... 260/243 D |
| 3,960,854 A | 6/1976 | Novello ................... 260/243 D |
| 3,973,038 A | 8/1976 | Umezawa et al. .......... 424/324 |
| 3,988,324 A | 10/1976 | Novello ................... 260/243 D |
| 4,021,556 A | 5/1977 | Springer et al. ............. 424/257 |
| 4,024,253 A | 5/1977 | Umezawa et al. ........... 424/230 |
| 4,058,614 A | 11/1977 | Baldwin ...................... 424/263 |
| 4,091,097 A | 5/1978 | Umezawa et al. .......... 424/230 |
| 4,179,512 A | 12/1979 | Baldwin et al. ............. 424/273 |
| 4,241,064 A | 12/1980 | Matsumura et al. .... 424/256 R |
| 4,281,005 A | 7/1981 | Baldwin ...................... 424/263 |
| 4,346,094 A | 8/1982 | Beck et al. .................. 424/270 |
| 4,495,195 A | 1/1985 | Beck et al. .................. 514/406 |
| 4,668,676 A | 5/1987 | Boswell et al. ............. 514/243 |
| 4,699,919 A | 10/1987 | Follet et al. ................. 514/431 |
| 4,912,092 A | 3/1990 | Gruber ........................ 514/45 |
| 4,920,119 A | 4/1990 | Attwood et al. ............. 514/243 |
| 4,978,668 A | 12/1990 | Babbs et al. ................. 514/258 |
| 5,013,756 A | 5/1991 | Follet et al. ................. 514/544 |
| 5,212,201 A | 5/1993 | Wakashiro et al. .......... 514/532 |
| 5,272,151 A | 12/1993 | Marzi et al. ................. 514/258 |
| 5,674,887 A | 10/1997 | Blake et al. ................. 514/407 |
| 5,785,993 A | 7/1998 | Baker et al. ................. 424/450 |
| 6,191,136 B1 * | 2/2001 | Marban ....................... 514/258 |

FOREIGN PATENT DOCUMENTS

| | | |
|---|---|---|
| CA | 997343 | 9/1976 |
| GB | 1134852 | 11/1968 |
| GB | 1301754 | 1/1973 |
| GB | 1358893 | 7/1974 |
| GB | 1372677 | 11/1974 |
| GB | 1373318 | 11/1974 |
| GB | 1378618 | 12/1974 |
| GB | 1416598 | 12/1975 |
| GB | 1427189 | 3/1976 |
| GB | 1427190 | 3/1976 |
| GB | 1451029 | 9/1976 |

OTHER PUBLICATIONS

T. Sisto et al., *Ann. Thorac. Surg.*, 59:1519–1523 (1995).
A. Movahed et al., *Can. J. Cariol.*, 12(2):138–144 (1996).
J. Coghlan et al., *Journal of Thoracic and Cardiovascular Surgery*, 11(1):248–256 (1994).
A. Bochenek et al., *European Journal of Cardiothoracic Surgery*, 4:538–542 (1990).
Kramer, et al. "Controlled Trial of Captopril in Chronic Heart Failure: A Rest and Exercise Hemodynamic Study", Circulation, vol. 67, No. 4, 1983, pp. 807–816.

\* cited by examiner

*Primary Examiner*—Kevin E. Weddington
(74) *Attorney, Agent, or Firm*—Peter F. Corless; Christine C. O'Day; Edwards & Angell, LLP

(57) ABSTRACT

The present invention relates to methods for modulating calcium sensitivity of cardiac muscle. In preferred aspects, the invention provides methods for enhancing myocardial contractility and cardiac performance, and methods for treatment of heart failure and other disorders associated with cardiac contractility by administration of one or more xanthine oxidase inhibitor compounds.

65 Claims, 9 Drawing Sheets

METHODS FOR TREATMENT OF DISORDERS OF CARDIAC CONTRACTILITY

CROSS-REFERENCE TO RELATED APPLICATION

This application is a divisional of U.S. application Ser. No. 09/186,755, filed Nov. 5, 1998, now issued as U.S. Pat. No. 6,191,136, which claims the benefit of U.S. provisional application No. 60/064,942, filed Nov. 7, 1997, which is incorporated by reference herein in its entirety.

The U.S. Government has certain rights in this invention as provided for by the terms of contract No. RO1 HL44065 awarded by the National Institutes of Health.

BACKGROUND OF THE INVENTION

1. Field of the Invention

The present invention relates to methods for modulating calcium sensitivity of cardiac muscle. In preferred aspects, the invention provides methods for enhancing myocardial contractility and cardiac performance, and methods for treatment of heart failure and other disorders associated with cardiac contractility by administration of one or more compounds that can increase cardiac contractility such as a xanthine oxidase inhibitor compound. The invention also provides methods for increasing cardiac contraction efficiency through administration of a xanthine oxidase inhibitor.

2. Background

Heart failure afflicts more than two million Americans, and congestive heart failure is recognized as the most common cause of hospitalization and mortality in Western society.

Congestive heart failure is a syndrome characterized by left ventricular dysfunction, reduced exercise tolerance, impaired quality of life and dramatically shortened life expectancy. Decreased contractility of the left ventricle leads to reduced cardiac output with consequent systemic arterial and venous vasoconstriction.

Captopril, enalapril and other inhibitors of angiotensin-converting enzyme (ACE) have been used to treat congestive heart failure. See Merck Index, 1759 and 3521 (11$^{th}$ ed. 1989); Kramer, B. L. et al. *Circulation* 1983, 67(4):755–763. However, such ACE inhibitors have generally provided only moderate or poor results. For example, captopril therapy generally provides only small increases in exercise time and functional capacity. Captopril also has provided only small reductions in mortality rates.

It thus would be desirable to have new therapies for treatment of heart failure.

SUMMARY OF THE INVENTION

The present invention includes methods for modulating, particularly increasing, calcium sensitivity of cardiac muscle. That is, the invention provides new methods for increasing contractile force of cardiac myofilaments, while decreasing intracellular calcium concentrations.

It has been surprisingly found that administration of a compound that can increase cardiac contractility, particularly a xanthine oxidase inhibitor compound, can sensitize cardiac muscle to intracellular calcium, and thus enable treatment of disorders associated with cardiac contractility. See, for instance, the results of the examples which follow.

Additionally, it has been unexpectedly found that xanthine oxidase inhibitor compounds can improve efficiency of cardiac contraction. In particular, it has been found that a xanthine oxidase inhibitor compound can induce a positive inotropic effect without increasing energy expenditure, thereby increasing mechanical efficiency. See the examples which follow.

Still further, it has been found that significantly elevated levels of xanthine oxidase activity may exist in subjects suffering from heart failure, relative to control subjects not suffering from heart failure. See, for instance, Example 6 below and FIG. 10 of the drawings, which details a four-fold increase in xanthine oxidase activity in subjects with heart failure, relative to controls. Those results indicate that xanthine oxidase inhibitors can act preferentially in heart failure patients, i.e. that xanthine oxidase inhibitors can boost contractility and efficiency more in failing than normal hearts.

More specifically, methods of the invention include treatment of disorders associated with cardiac contractility, particularly heart failure including congestive heart failure and cardiogenic shock. In one aspect, the treatment methods of the invention in general comprise administration of a therapeutically effective amount of one or more compounds that can increase cardiac contractility to a patient in need of treatment, such as a mammal, particularly a primate such as a human. Preferred compounds for administration include those that inhibit xanthine oxidase (a xanthine oxidase inhibitor).

The invention also includes methods for improving efficiency of cardiac contraction to a patient in need of such treatment. These methods in general comprise administration of an effective amount of a xanthine oxidase inhibitor compound to the patient, particularly an effective amount of allopurinol or oxypurinol. Preferably, a patient will be identified and selected for such treatment, e.g. a patient that is suffering heart failure, including congestive heart failure, where an increase in myocardial contractility with reduced energy requirements is an intended desired therapy.

The methods of the invention include both acute and chronic therapies.

For example, a xanthine oxidase inhibitor can be immediately administered to a patient (e.g. i.p. or i.v.) that has suffered or is suffering from congestive heart failure or cardiogenic shock. Such immediate administration preferably would entail administration of a xanthine oxidase inhibitor within about 1, 2, 4, 8, 12 or 24 hours, or from more than one day to about 2 or three weeks, after a subject has suffered from heart failure such as congestive heart failure or cardiogenic shock.

Relatively long-term administration of a therapeutic agent also will be beneficial after a patient has suffered from chronic heart failure to provide increased exercise tolerance and functional capacity. For example, a xanthine oxidase inhibitor can be administered regularly to a patient for at least 2, 4, 6, 8, 12, 16, 18, 20 or 24 weeks, or longer such 6 months, 1 years, 2 years three years or more, after having suffered heart failure to promote enhanced functional capacity. An oral dosage formulation would be preferred for such long-term administration.

A wide variety of compounds, including xanthine oxidase inhibitors, can be employed in the methods of the invention. For example, suitable xanthine oxidase inhibitor compounds have been previously reported including the compounds disclosed in U.S. Pat. Nos. 5,674,887; 5,272,151; 5,212,201; 4,495,195; 4,346,094; 4,281,005; 4,241,064; 4,179,512; 4,058,614; 4,024,253; 4,021,556; 3,920,652; 3,907,799; 3,892,858; 3,892,738; 3,890,313; 3,624,205; 3,474,098; and 2,868,803.

Specifically preferred therapeutic compounds for use in the methods of the invention include allopurinol (4-hydroxypyrazolo[3,4-d]pyrimidine) and oxypurinol (4,6-dihydroxypyrazolo[3,4-d]pyrimidine), and pharmaceutically acceptable salts of those compounds.

Other aspects of the invention are disclosed below.

BRIEF DESCRIPTION OF THE DRAWINGS

FIGS. 5–8 show graphically the results of Example 4. In FIGS. 5–7, squares in plot represent control dogs and circles in plots represent heart failure dogs.

FIG. 5 shows graphically the results of Example 4 which follows, specifically the effect of allopurinol on relation between stroke work and end-diastolic dimension (preload recruitable stroke work).

FIG. 8 show graphically the results of Example 4 which follows, specifically representative tracings of left circumflex blood velocity before and 10 minutes after 200 mg allopurinol i.v. administration over 30 minutes in a heart failure dog.

DETAILED DESCRIPTION OF THE INVENTION

Figure 1:
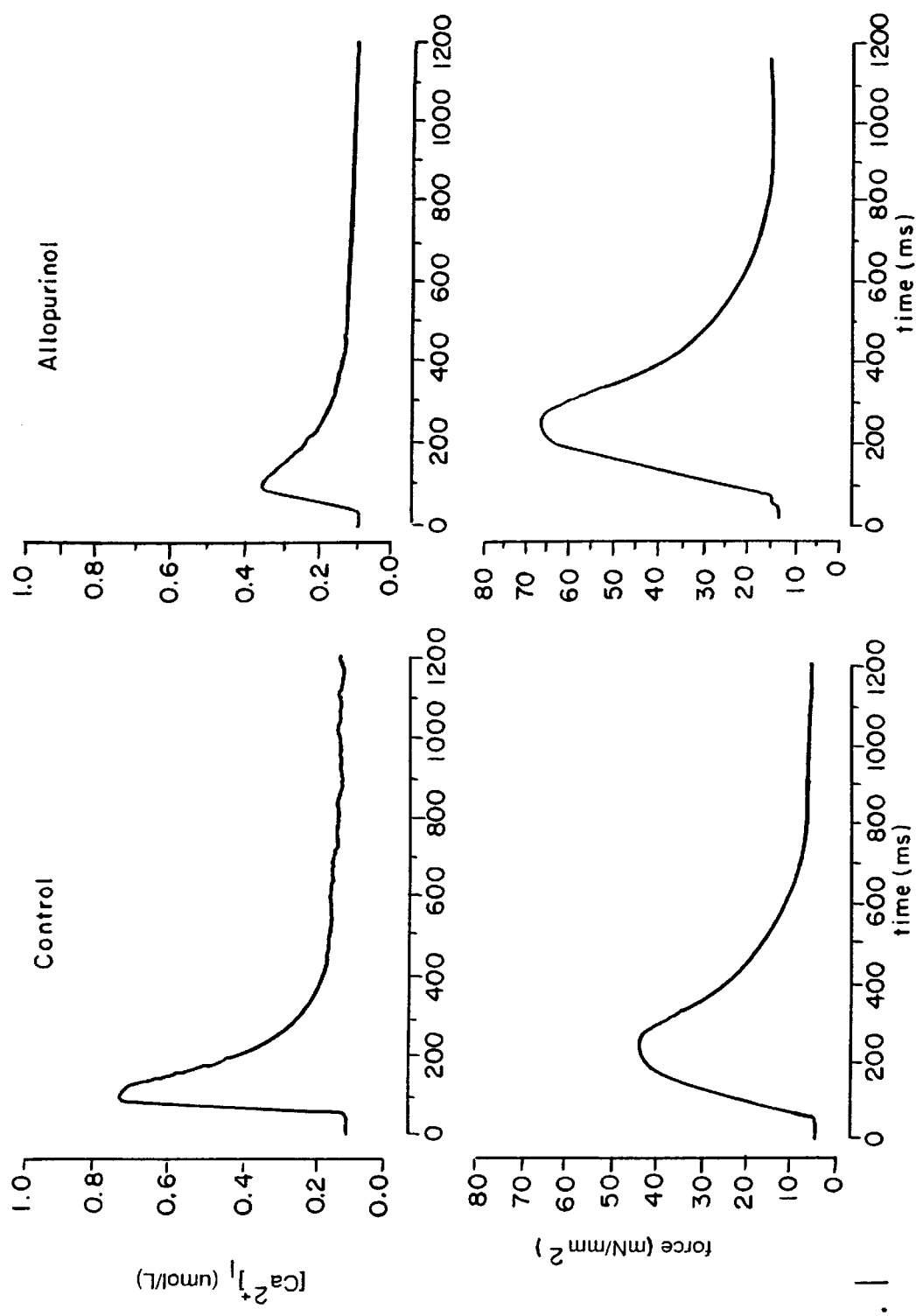
FIG. 1 shows graphically the results of Example 1 which follows, specifically the effects of allopurinol on the contractile force (lower panel) and calcium ion concentration of cardiac muscle relative to a control that was not exposed to allupurinol.

As stated above, and demonstrated in the examples which follow, it has now been found that administration of a compound that can increase cardiac contractility, particularly a xanthine oxidase inhibitor compound, to a subject can sensitize cardiac muscle to intracellular calcium ions ($[Ca^{2+}]_i$). Calcium is the intracellular chemical signal that initiates contraction by binding to cardiac myofilaments. Thus, xanthine oxidase inhibitors which increase calcium sensitivity of cardiac myofilaments can boost contractility without imparting a primary effect on calcium cycling properties of heart cells.

It is believed the methods of the invention are further unique in that cardiac myofilaments are sensitized to calcium without altering cyclic AMP levels by phosphodiesterase inhibition.

It is also believed that preferred methods of the invention can sensitize myofilaments to $Ca^{2+}$ to cause cardiac myocytes to generate more force for a given amount of cytoplasmic free $Ca^{2+}$. In this regard, it should be appreciated that myocyte $Ca^{2+}$+cycling can be slowed and blunted during heart failure.

Moreover, as discussed above, it has been found that preferred xanthine oxidase inhibitor compounds can improve efficiency of cardiac contraction. See the results set forth in the examples which follow.

The methods of the invention in general comprise administration of a therapeutically effective amount of one or more compounds that can increase cardiac contractility, particularly a xanthine oxidase inhibitor compounds. Allopurinol and oxypurinol are particularly preferred agents.

Typical subjects for treatment include persons susceptible to, suffering from or that have suffered a disorder associated with cardiac contractility. In particular, suitable subjects for treatment in accordance with the invention include persons that are susceptible to, suffering from or that have suffered heart failure, particularly congestive heart failure or acute cardiogenic shock. The efficacy of any particular therapeutic agent the treatment methods of the invention can be readily determined. For example, suitable compounds can be identified through the in vitro calcium-sensitizing assay as disclosed in Example 1 which follows, and which includes the following steps a) through c): a) mounting dissected rat cardiac specimens in a tissue bath in which fura-2 has been microinjected into the tissue to enable measurement of intracellular calcium concentration ($[Ca^{2+}]_i$), b) adding a candidate therapeutic compound to the tissue bath, c) measuring contractile force and/or $[Ca^{2+}]_i$ of the cardiac specimen both before and after addition of the candidate compound. References herein to a standard in vitro calcium-sensitizing assay refers to that protocol of steps a) through c).

Preferred compounds for use in the therapeutic methods of the invention induce at least about a 3% or 5% increase in cardiac contractile force relative to contractile force measured in absence of the tested compound in such a standard in vitro calcium-sensitizing assay, more preferably at least about a 10% or 15% increase in cardiac contractile force relative to a control, and still more preferably induce at least about 20%, 30%, 40%, 50%, 60%, 70%, 80%, 90% or 100% increase in cardiac contractile force relative to absence of the tested compound in such a standard in vitro calcium-sensitizing assay.

Even more preferred compounds for use in the present therapeutic methods induce such increases in contractile force, and further induce a decreased intracellular calcium concentration ($[Ca^{2+}]_i$). Preferably, such compounds induce at least about a 3% or 5% decrease in intracellular calcium concentration relative to intracellular calcium concentration measured in absence of the compound in such a standard in vitro calcium-sensitizing assay, more preferably at least about a 10 or 15% decrease in intracellular calcium concentration, and still more preferably induce at least about 20%, 25%, 30%, 40% or 50% decrease in intracellular calcium concentration relative to intracellular calcium concentration measured in absence of the therapeutic compound in such a standard in vitro calcium-sensitizing assay. Such decrease in intracellular calcium concentration would be expected to be an energy saving effect.

Even more preferred compounds for use in the methods of the invention are those that improve efficiency of cardiac contraction. Preferably such compounds can induce at least about a 5% or 10% increase in preload-recruitable stroke work (PRSW) in heart failure dogs relative to control dogs (no therapeutic compound administered) with PRSW values measured at 30 minutes after test compound administration, more preferably at least about a 15%, 20%, 30%, 40%, 50%, or even about 55%, 60% or 70% increase in PRSW in heart failure dogs relative to control dogs with PRSW values measured at 30 minutes after test compound administration, and with PRSW values determined in a standard in vivo dog pacing induced heart failure model as such model is described in Example 5 which follows and includes the following steps a) through c): a) inducing heart failure in dogs by chronic rapid ventricular pacing, b) infusing a xanthine oxidase inhibitor, such as allopurinol or oxypurinol, into the right atrium of the test dogs at a rate of 3.3 mL/min. at a properly determined dosage, c) recording the pressure-dimension relationships and the arterial pressure response. References herein to a "standard in vivo dog pacing induced heart failure model" designate a protocol as described in Example 5 below and including those steps a) through c).

As discussed above, xanthine oxidase inhibitors are particularly preferred for use in the treatment methods of the invention. The ability of a particular candidate compound to inhibit xanthine oxidase can be assessed by known protocols, such as the following. This following described protocol is referred to herein as "a standard in vitro xanthine oxidase assay": Xanthine oxidase can be obtained from known sources such as from rat liver according to method disclosed in Della Corte, E. et al., *Biochem J* 1970, 117:97, and aged for at least 24 hours prior to use. Solutions of 3 ml of 0.1M aqueous tris hydrochloride buffer (pH 8.1) containing $10^{-5}$ M xanthine are treated with 200 $\mu$l of xanthine oxidase dissolved in 0.1 M aqueous tris hydrochloride buffer (pH 8.1) and incubated at 30° C. in the presence and absence of a candidate compound, and where the formation of uric acid from xanthine is monitored by measuring light absorption at 293 nm. The $IC_{50}$ (concentration of candidate compound to provide 50% inhibition of xanthine oxidase-catalyzed oxidation of xanthine to uric acid) then can be determined. Xanthine oxidase inhibitors generally suitable for purposes of the invention will exhibit a detectable inhibition of the xanthine oxidase-catalyzed oxidation of xanthine to uric acid in the above assay, and preferably will exhibit an $IC_{50}$ of at least about 1 mM, more preferably an $IC_{50}$ about 100 mM in that assay.

As mentioned above, in one aspect, the methods of the invention in general comprise administration of a therapeutically effective amount of one or more compounds that can increase cardiac contractility, such as xanthine oxidase inhibitor compounds. Compounds that exhibit in vitro activity may then be further evaluated. The in vivo efficacy of any particular therapeutic agent in the treatment methods of the invention can be readily determined. For example, suitable compounds can be identified through the in vivo induced heart failure model as disclosed in Example 5 which follows, and which includes the following steps a) through c) as also discussed above: a) inducing heart failure in a dog by chronic rapid ventricular pacing, b) infusing a xanthine oxidase inhibitor, such as allopurinol or oxypurinol, into the right atrium at a rate of 3.3 mL/min. at a properly determined dosage, c) recording the pressure-dimension relationships and the arterial pressure response. Cardiac oxygen consumption also may be measured as disclosed in Example 5.

In addition to the above discussed xanthine oxidase inhibitors, suitable inhibitor compounds for use in the methods of the invention are disclosed below. It should be appreciated however that the present invention is not limited by the particular xanthine oxidase inhibitor, and the invention is applicable to any such xanthine oxidase inhibitor compound now known or subsequently discovered or developed.

More specifically, suitable compounds to use in the treatment methods of the invention include compounds of the following Formulae I and II:

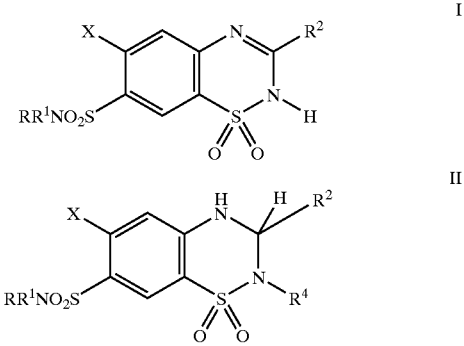

and pharmacologically acceptable salts thereof wherein R, $R^1$ and $R^4$ are similar or dissimilar groups selected from hydrogen and lower alkyl having from 1 to about 5 carbon atoms, X is selected from halogen, particularly chloro or bromo, trifluoromethyl, and lower alkyl having advantageously from 1 to 3 carbon atoms and $R^2$ is a diazine attached through one of its carbon atoms to the benzothiadiazine nucleus and optionally mono- or di-substituted with similar or dissimilar groups selected from $C_{1-3}$ alkyl, halo, preferably chloro and bromo, lower alkoxy and hydroxy. The diazine substituent is derived from a pyrazine, pyridazine or pyrimidine and attachment to the benzothiadiazine nucleus can be through any of the available carbons of the diazine nucleus: Compounds of the above Formula I and II can be suitably synthesized prepared through any of the known procedures for making benzothiadiazine compounds (for compounds of Formula I) or 3,4-dihydrobenzothiadiazine compounds (for compounds of Formula II). See also U.S. Pat. No. 3,890,313.

Additional suitable compounds for use in the methods of the invention include those of the following Formula III:

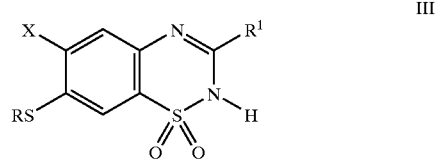

and pharmacologically acceptable salts thereof wherein X represents halo (preferably chloro), $C_{1-3}$-alkyl (particularly methyl) and trifluoromethyl; R represents hydrogen, a straight or branched chain lower alkyl having from 1 to 6 carbon atoms and phenyl-lower alkyl having from 1 to 3 carbon atoms (preferably benzyl); $R^1$ represents hydrogen, lower alkyl having from 1 to 5 carbon atoms or substituted lower alkyl wherein the substituent is mono or dihalo (preferably chloro), and phenyl, the group —$CO_2$ lower alkyl having from 1 to 5 carbon atoms, an azine optionally substituted with one or more lower alkyl having 1 to 3 carbon atoms or a diazine optionally substituted with one or more lower alkyl having from 1 to 3 carbon atoms, or the group —CONR$^2$R$^3$ wherein R$^2$ and R$^3$ can be similar or dissimilar and selected from hydrogen, lower alkyl having 1 to 5 carbon atoms or hydroxy substituted lower alkyl having 1 to 5 carbon atoms. Compounds of Formula III can be suitably prepared by known methods. See, in particular, the procedures disclosed in U.S. Pat. No. 3,892,738.

Additional compound that will be useful in the methods of the invention include compounds of the following Formula IV:

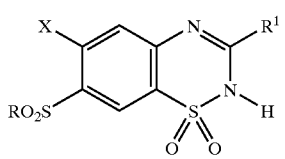

IV and pharmaceutically acceptable salts thereof wherein X represents halo (preferably chloro), $C_{1-3}$-alkyl (particularly methyl) and trifluoromethyl; R represents a straight or branched chain lower alkyl having from 1 to 6 carbon atoms and phenyl-lower alkyl having from 1 to 3 carbon atoms (preferably benzyl); R$^1$ represents (1) hydrogen, (2) lower alkyl having from 1 to 5 carbon atoms or substituted lower alkyl wherein the substituent is mono, di- or trihalo (preferably chloro), and phenyl, (3) the group —CO$_2$R$^2$ wherein R-2- is hydrogen or lower alkyl having from 1 to 5 carbon atoms, (4) the group —CONH$_2$ or (5) an azine optionally substituted with one or more lower alkyl having 1 to 3 carbon atoms or a diazine optionally substituted with one or more lower alkyl having from 1 to 3 carbon atoms. Compounds of Formula IV can be suitably prepared by known methods for making benzothiadiazine compounds. See, in particular, the procedures disclosed in U.S. Pat. No. 3,892,858.

Additional useful compounds for use in the methods of the invention include imidazo [1,2,a] and pyrazolo[1,5,a] pyrimidine compounds, particularly those of the following Formula V:

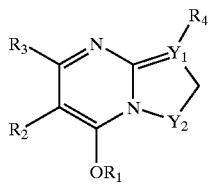

V $Y_1$ and $Y_2$ are carbon or nitrogen; $R_1$ is H or an alkali metal or ammonium; $R_2$ is H, CH$_3$, a halogen, phenylazo or NO$_2$;

$R_3$ is OR$_1$, H, or a halogen; and $R_4$ is H, NO$_2$ or a halogen. When $Y_1$ is carbon, $Y_2$ is nitrogen, thereby formning the pyrazolo compounds, and when $Y_1$ is nitrogen, $Y_2$ is carbon, thus providing the imidazo compounds. Such imidazo [1,2,a] and pyrazolo[1,5,a]pyrimidine compounds can be synthesized by known procedures. See, in particular, the procedures disclosed in U.S. Pat. No. 3,907,799.

Additional suitable pyrazolo[1,5a]pyrimidine compounds for use in the methods of the invention include compounds of the-following Formula VI:

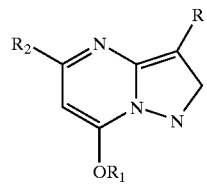

VI

R is an aromatic or substituted aromatic nucleus, as for example, phenyl, naphthyl, tolyl, halogenated phenyls, heterocyclic nucleus, etc., R$_1$ is H, an alki metal or ammonium, and R$_2$ is H or OR$_1$. Examples of suitable R substituents include phenyl, 1-naphthyl, substituted phenyls of the formula VIa

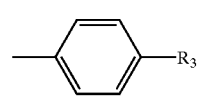

VIa where R$_3$ is CH$_3$, a halogen, or

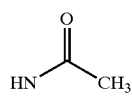

VIb m-tolyl, heterocyclic nucleus as for example

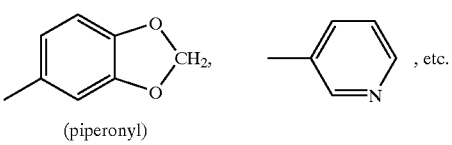

VIc (piperonyl)

$R_1$ is preferably H thus yielding 5,7-dihydroxy pyrazolo[1,5a] pyrimidines where $R_2$ is OR$_1$, although physiologically acceptable salts as for example, alkali metal or ammonium, may also be used. Again, such pyrazolo[1,5,a]pyrimidine compounds can be synthesized by known procedures, e.g. as disclosed in U.S. Pat. No. 3,920,652.

Additional compounds useful in the methods of the invention include those of the following Formula VII:

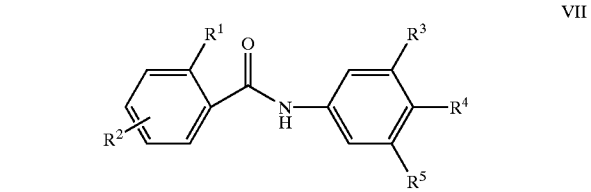

VII wherein
R$^1$ is

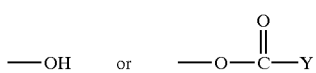

in which Y is lower alkyl or phenyl;
R$^2$ is substituted either at the 4'-position or at the 5'-position and is hydrogen, fluoro, bromo, chloro, hydroxy, lower alkyl or

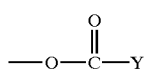

in which Y is lower alkyl or phenyl;
$R^3$ is chloro, bromo or lower alkyl;
$R^4$ is hydroxy, amine, lower alkoxy or

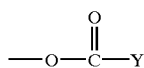

in which Y is lower alkyl or phenyl;
$R^5$ is hydrogen, fluoro, bromo, chloro, carboxyl, lower alkyl or

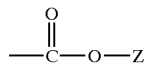

in which Z is lower alkyl; and the nontoxic, pharmaceutically acceptable metal salts of said compound in which $R^5$ is carboxyl. Compounds of Formula VII may be suitably prepared as described in U.S. Pat. No. 4,024,253.

Additional suitable compounds for use in the methods of the invention include substituted imidazole compounds of the following Formula VIII:

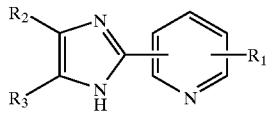

wherein
$R_1$ is hydrogen or alkyl containing 1 to 3 carbon atoms;
$R_2$ is halogen; and
$R_3$ is halogen or —$CF_3$;
or a pharmaceutically acceptable salt thereof. Preferred compounds of Formula VII include those where $R_1$ is hydrogen, $R_2$ is chlorine or bromine and $R_3$ is chlorine, bromine or $CF_3$. Compounds of Formula VIII may be suitably prepared as described in U.S. Pat. No. 4,058,614.

Further suitable compounds for use in the methods of the invention include 2,4(5)disubstituted imidazoles, including compounds of the following Formulae IX and X:

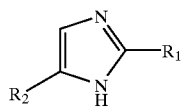

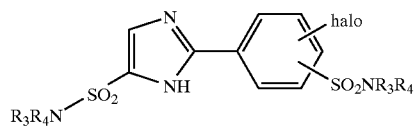

and pharmaceutically acceptable salts thereof wherein:
$R_1$ is selected from the group consisting of monohalo (e.g. Cl, Br, I or F)-phenyl, dihalo(e.g. Cl or Br)-phenyl and pyridyl (e.g. 3-pyridyl, 4-pyridyl),
halo is Cl, Br, I or F $R_2$ is selected from the group consisting of $C_1$–$C_5$ alkyl-S—, $C_1$–$C_5$ alkyl-SO—, $C_1$–$C_5$ alkyl-$SO_2$— and $R_3R_4N$—$SO_2$—, and
$R_3$ and $R_4$ are independently selected from H, $C_1$–$C_5$ alkyl and hydroxy substituted $C_2$–$C_5$ alkyl. The alkyl moiety in the $R_2$ groups defined above includes branched or straight chain alkyl groups such as $CH_3$—, t-butyl, n-pentyl and the like. The hydroxy substituted $C_2$–$C_5$ alkyl groups are also branched and straight chain alkyls having 1–2 hydroxy groups—the monohydroxy straight chain alkyls are preferred e.g. —$CH_2$—CHOH—$CH_3$ and —$(CH_2)_5$—OH. Compounds of Formulae IX and X may be suitably prepared as described in U.S. Pat. No. 4,179,512. That patent also disclose preferred compounds of the above formulae, identified as compounds of formulae II and III in U.S. Pat. No. 4,179,512.

Additional suitable compounds for use in the methods of the invention include 1-substituted-9H-pyrido[3,4-b]indole compounds, including compounds of the following Formula XI:

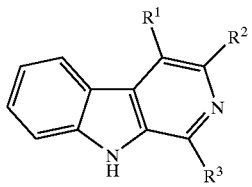

wherein
one of $R^1$ and $R^2$ is hydrogen and the other is hydrogen, hydroxy or —$OR^4$ wherein $R^4$ is alkanoyl of 2 to 7 carbon atoms, tosyl or mesyl and
$R^3$ is hydroxymethyl, formyl, carboxy or carbalkoxy wherein alkoxy contains 1 to 6 carbon atoms. In that formula X, the term "alkanoyl of 2 to 7 carbon atoms" refers to a group of the formula $(C_xH_{2x+1})CO$ wherein x has a value of 1 to 6, e.g. acetyl, propionyl, butyryl and the like. Alkoxy of 1 to 6 carbon atoms refers to the group $(C_xH_{2x+1})$—O— wherein x is again 1 to 6. Compounds of Formula XI may be suitably prepared as described in U.S. Pat. No. 4,241,064.

Further compounds suitable for use in the methods of the invention include compounds of the following Formulae XII through XV:

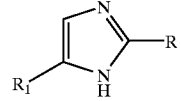

wherein in Formula XII, R is 3-pyridyl or 4-pyridyl and $R_1$ is $C_1$–$C_5$ alky, branched or unbranched, e.g. t-butyl, n-pentyl, isopropyl, and pharmaceutically acceptable salts thereof;

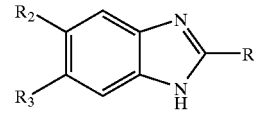

wherein in Formula XIII, R is 3-pyridyl or 4-pyridyl, $R_2$ is bromo or chloro, and $R_3$ is hydrogen, bromo or chloro, and pharmaceutically acceptable salts thereof; and

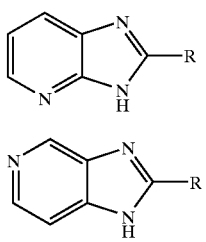

XIV

XV wherein in each of Formula XIV and XV, R is 3-pyridyl or 4-pyridyl, and pharmaceutically acceptable salts thereof. Compounds of those Formula XI through XIV can be suitably prepared as disclosed in U.S. Pat. No. 4,281,005.

Additional suitable compounds include 3-aryl-5-isothiazoles, including compounds of the following Formula XVI:

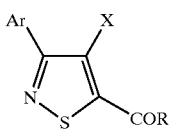

XVI wherein

Ar is pyridyl, thienyl, phenyl or

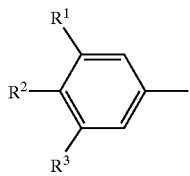

wherein $R^1$, $R^2$ and $R^3$ are individually H, $CF_3$, halogen, alkyl or O-alkyl or $R^1$ and $R^2$ or $R^2$ and $R^3$ when taken together are methylenedioxy;

X is $NH_2$, H, halogen, OH or NH-alkyl;

R is OH, OM, O-alkyl, $NH_2$, NH-alkyl or $N(alkyl)_2$;

wherein halogen is Cl, F, I, or Br; and M is a nontoxic cation, preferably an alkali metal cation such as K or Na, an alkaline earth metal cation such as Mg or Ca, another nontoxic metal cation such as Al or Zn or a nontoxic metalloid cation such as $NH_4^+$, piperazinium, 2-hydroxyethylammonium and the like. In that Formula XVI, alkyl is preferably lower alkyl such as ($C_1$–$C_3$) alkyl including methyl, ethyl, n-propyl or isopropyl. Compounds of Formula VXI may be suitably prepared as described in U.S. Pat. No. 4,346,094.

Additional suitable compounds useful in the methods of the invention include substituted pyrazole compounds, particularly those of the following Formulae XVII, XVIII and XIX:

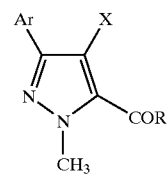

XVII

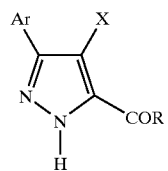

XVIII

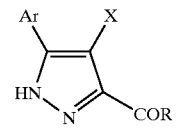

XIX wherein Ar is pyridyl, thienyl or

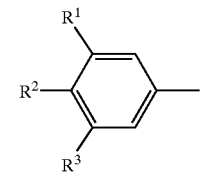

wherein
$R^1$, $R^2$ and $R^3$ are individually H, $C_{1-3}$ haloalkyl, F, Br, Cl, I, $Cl_{1-3}$ alkyloxy, $R^1$ and $R^2$ or $R^2$ and $R^3$ taken together represent methylmedioxy, provided at least one of $R^1$, $R^2$ and $R^3$ is H, one of $R^1$, $R^2$ and $R^3$ is other than H and only one of $R^1$, $R^2$ and $R^3$ can be I;
R is OH, OM, $NH_2$, N-alkyl, $N(alkyl)_2$, O-alkyl or N-alkenyl-$N(alkyl)_2$;
X is $NH_2$, OH, H, F, Cl, Br, I or $C_{1-3}$ alkyl; alkyl is $C_{1-5}$ alkyl; alkenyl is $(CH_2)_2$ or $(CH_2)_3$; and M is a nontoxic cation. It should be appreciated that compounds of the above Formula XVIII and XIX can exist as a corresponding tautomeric pair, i.e. as a 3-aryl-pyrazole-5-carboxylic acid and a 5-arylpyrazole-3-carboxylic acid. Also, when one or more of $R^1$, $R^2$ or $R^3$ substituents of Formulae XVII, XVIII and XIX are $C_{1-3}$ haloalkyl derivatives, preferably such group will be fully halogenated such as in a trifluoromethyl or pentachloroethyl group. Such a fully halogenated alkyl radical is more stable than partially-halogenated haloalkyl radicals and maintain their structural integrity during most synthetic procedures. A preferred group of compounds of Formula XVII, XVIII and XIX are those where Ar is substituted phenyl, in particular 3 or 4-trifluoromethylphenyl, 3 or 4-chlorophenyl, 3 or 4-bromophenyl or 3 or 4-methoxyphenyl. Compounds where Ar is 3-trifluoromethylphenyl are especially preferred. Also preferred are those compounds of Formulae XVII, XVIII and XIX in which X is H, OH or $NH_2$, and particularly preferred compounds include those where X is H. Still further preferred are those compounds of Formulae XVII, XVIII and XIX that are free acids (R=OH) or pharmaceutically-acceptable salts thereof (M is a non-toxic cation). The term "$C_{1-5}$ alkyl"

as used in reference to Formulae XVII, XVIII and XIX includes such radicals as methyl, ethyl, n-propyl, isopropyl, n-butyl, isobutyl, sec-butyl, 1-pentyl, 2-pentyl, 3-pentyl, 3-pentyl, 3-methyl-1-butyl, 3-methyl-2-butyl and the like. The term "$C_{1-3}$ alkyl" as used in reference to Formulae XVII, XVIII and XIX includes methyl, ethyl, n-propyl and isopropyl.

The term "$C_{1-3}$ haloalkyl" as used in reference to Formulae XVII, XVIII and XIX designates halogenated derivations of the $C_{1-3}$ alkyl radicals listed above and includes such radicals as trifluoromethyl, trichloromethyl, difluoromethyl, chlorodifluoromethyl, bromomethyl, α,α-difluoroethyl, pentafluoroethyl, heptafluoro-n-propyl, pentachloroethyl, iodomethyl, etc. Preferred pharmaceutically-acceptable salts of compounds of Formula XVII, XVIII and XIX include those formed with a non-toxic cation, preferably an alkali metal cation such as K or Na, an alkaline earth metal cation such as Mg or Ca, another non-toxic metal cation such as Al or Zn or a non-toxic metalloid cation such as $NH_4^+$, piperazinium or 2-hydroxyethylammonium. Compounds of Formulae XVII, XVIII and XIX may be suitably prepared by methods disclosed in U.S. Pat. No. 4,495,195.

Further compounds suitable for use in the methods of the invention include those of the following Formula XX:

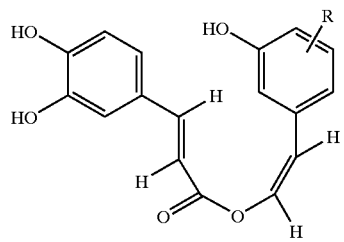

XX wherein R is 4'-OH or 5'-OH, or a pharmaceutically acceptable salt thereof. Methods for obtaining compounds of Formula XX are disclosed in U.S. Pat. No. 5,212,201.

Additional suitable compounds for use in the methods of the invention include aminoacyl and oligopeptidyl derivatives of allopurinol of the following Formula XXI:

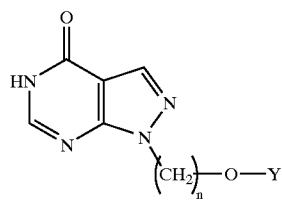

XXI and pharmaceutically acceptable salts thereof with pharmacologically-acceptable cations, and in which above formula n is an integer between 2 and 6, preferably 5, Y is H or CO—A, in which A is a racemic or chiral amino acid, dipeptide, tripeptide, tetrapeptide, or pentapeptide chose, respectively, from the groups consisting of:

a) arginine, aspartic acid, lysine, leucine;

b) glycylaspartate, glycylglycine, aspartylarginine, leucylarginine, alanylglycine;

c) arginyllysylaspartate, aspartyllysylarginine, lysylprolylarginine, prolylprolylarginine, lysylhistidylglycinamide, prolylphenylalanylarginine, phenylalanylprolylarginine;

d) arginyllysylaspartylvaline, valylaspartyllysylarginine, threonylvalylleucylhistidine;

e) arginyllysylaspartylvalyltyrosine. For the purposes of Formula XXI, "amino acid, dipeptide, tripeptide, tetrapeptide, or pentapeptide" are taken to mean an amino acid, dipeptidyl, tripeptidyl, tetrapeptidyl, or pentapeptidyl moiety bonded to a CO group by an amino nitrogen. By "pharmacologically-acceptable cations" is meant cations such as sodium, potassium, magnesium, ammonium, and whichever other cations experts in the field may elect to designate a pharmacologically acceptable. Compounds of Formula XXI can be readily prepared by known methods such as disclosed in U.S. Pat. No. 5,272,151.

Additional suitable compounds for use in the methods of the invention include pyrazolotriazine compounds, particularly those of the following Formula XXII:

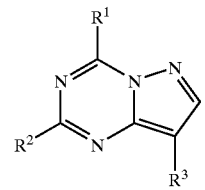

XXII wherein $R^1$ is hydroxy or a lower alkanoyloxy, $R^2$ is hydrogen atom, hydroxy, or mercapto, $R^3$ is (1) an unsaturated heterocyclic group containing nitrogen or sulfur atom as the hetero atom, which may optionally have one or two substituents selected from a halogen atom, nitro, and phenylthio, (2) naphthyl, (3) a phenyl which may optionally have one to three substituents selected from the group consisting of (i) a lower alkyl, (ii) phenyl, (iii) a lower alkoxycarbonyl, (iv) cyano, (v) nitro, (vi) a lower alkoxy, (vii) a phenyl-lower alkoxy, (viii) a phenylthio-lower alkyl, (ix) phenoxy, (x) a group of the formula:

wherein R is a lower alkyl, a halogen-substituted lower alkyl, a phenyl which may optionally have one to three substituents selected from a halogen atom, a lower alkyl and a lower alkoxy, or pyridyl, and 1 is an integer of 0, 1 or 2, (xi) a halogen atom, (xii) a phenyl-lower alkyl, (xiii) carboxy, (xiv) a lower alkanoyl, (xv) a benzoyl which may optionally have one to three substituents selected from a halogen atom, a phenoyl-lower alkoxy and hydroxy on the phenyl ring, (xvi) amino, (xvii) hydroxy, (xviii) a lower alkanoyloxy, (xix) a group of the formula:

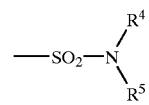

wherein $R^4$ and $R^5$ are the same or different and are each hydrogen atom, a cycloalkyl, a lower alkyl which may optionally have a substituent selected from hydroxy, furyl, thienyl, tetrahydrofuranyl and phenyl, a phenyl which may optionally have one to three substituents selected from a lower alkyl, a hydroxy-substituted lower alkyl, a lower alkanoyl, cyano, carboxy, a lower alkoxycarbonyl, hydroxy, a lower alkoxy, and a halogen atom, or a heterocyclic group selected from pyridyl, pyrimidinyl, thiazolyl, isoxazolyl, and pyrazolyl, said heterocyclic group being optionally substituted by a lower alkyl, amino, or a lower alkanoylarnino, or $R^4$ and $R^5$ may join together with the adjacent nitrogen atom to form a saturated 5- or 6-membered heterocyclic group which may optionally be intervened with oxygen atom, or (xx) a group of the formula:

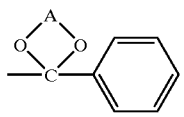

wherein A is a lower alkylene.

In the above Formula XXII, the identified groups include specifically the following groups. The "lower alkyl" includes alkyl groups having 1 to about 6 carbon atoms, for example, methyl, ethyl, propyl, isopropyl, butyl, t-butyl, pentyl, hexyl, etc. The "halogen atom" includes, for example, fluorine, chlorine, bromine, and iodine. The "lower alkoxy" includes alkoxy groups having 1 to about 6 carbon atoms, for example, methoxy, ethoxy, propoxy, isopropoxy, butoxy, t-butoxy, pentyloxy, hexyloxy, etc. The "lower alkoxy", "lower alkanoyloxy" and "lower alkanoylamino" include as the lower alkanoyl moiety alkanoyl groups having 1 to about 6 carbon atoms, for example, formyl, acetyl, propionyl, butyryl, isobutyryl, valeryl, isovaleryl, pivaloyl, hexanoyl, etc. The "unsaturated heterocyclic group containing nitrogen or sulfur atom as the hetero atom" includes monocyclic or condensed heterocyclic groups containing nitrogen or sulfur atom, for example, pyrrolyl, pyridyl, thienyl, thiopyranyl, indolyl, benzothienyl, 2,3-dihydrobenzothienyl, thiochromanyl, dibenzothienyl, etc. The heterocyclic group may optionally have one or two substituents selected from a halogen atom, nitro and phenylthio. Suitable examples of the heterocyclic group are, for example, 2-pyrrolyl, 3-pyrrolyl, 2-pyridyl, 3-pyridyl, 4-pyridyl, 2-thienyl, 3-thienyl, 2-thiopyranyl, 3-thiopyranyl, 4-thiopyranyl, 5-chloro-2-thienyl, 5-bromo-2-thienyl, 4-bromo-2-thienyl, 2-bromo-3-thienyl, 2,5-dichloro-3-thienyl, 2,5-dibromo-3-thienyl, 4,5-dibromo -2-thienyl , 4,5-dibromo-3-thienyl, 2-chloro-5-pyridyl, 2,3-dibromo-5-pyridyl, 5-nitro-2-thienyl, 4-nitro-2-thienyl, 3-nitro-2-thienyl, 2-nitro-3-thienyl, 2-nitro-4-pyridyl, 6-nitro-2-pyridyl, 3-phenylthio-2-thienyl, 5-phenylthio-2-thienyl, 5-phenylthio-3-thienyl 4-phenylthio-2-pyridyl, 5-phenylthio-2-pyridyl, 1-indolyl, 2-indolyl, 3-indolyl, 4-indolyl, 5-indolyl, 6-indolyl, 7-indolyl, 1-benzothiophen-2-yl, 1-benzothiophen-3-yl, 1-benzothiophen-4-yl, 1-benzothiophen-5-yl, 1-benzothiophen-6-yl, 1-benzodihydro-1-benzothiophen-5-yl, 2,3-dihydro-1-benzothiophen-6-yl, 2,3-dihydro-1-benzothiophen-7-yl, thiochroman-5-yl, thiochroman-6-yl, thiochroman-7-yl, thiochroman-8-yl, dibenzothiophen-1-yl, dibenzothiophen-2-yl, dibenzothiophen-3-yl, dibenzothiophen-4-yl, etc. The term "naphthyl" includes, for example, 1-naphthyl, 2-naphthyl, etc. The term "lower alkoxycarbonyl" includes alkoxycarbonyl groups having 1 to about 6 carbon atoms in the alkoxy moiety, for example, methoxycarbonyl, ethoxycarbonyl, propoxycarbonyl, isopropoxycarbonyl, butoxycarbonyl, t-butoxycarbonyl, pentyloxycarbonyl, hexyloxycarbonyl, etc. The term "phenyl-lower alkoxy" includes phenylalkoxy groups having 1 to about 6 carbon atoms in the alkoxy moiety, for example, benzyloxy, 1-phenylethoxy, 2-phenylethoy, 3-phenylpropoxy, 2-phenyl-1-methylethoxy, 4-phenylbutoxy, 2-phenyl-1, 1-dimethylethoy, 5-phenyl-pentyloy, 6-phenylhexyyloxy, etc. The term "phenylthio-lower alkyl" includes phenylthioalkyl groups having 1 to about 6 carbon atoms in the alkyl moiety, for example, phenylthiomethyl, 1-phenylthioethyl, 2-phenylthioethyl, 3-phenylthiopropyl, 2-phenylthio-1-methylethyl, 4-phenylthiobutyl, 2-phenylthio-1, 1-dimethylethyl, 5-phenylthiopentyl, 6-phenylthiohexyl, etc. The term "halogen-substituted lower alkyl" includes halogen-substituted alkyl groups having 1 to about 6 carbon atoms in the alkyl moiety, for example, chloromethyl, bromo-methyl, 1-chloroethyl, 2-chloroethyl, 2-bromoethyl, 3-chloropropyl, 2-chloro-1-methylethyl, 2-bromobutyl, 4-bromobutyl, 2-chloro-1, 1-dimethylethyl, 5-chloropentyl, 6-bromohexyl, etc. The term "phenyl which may optionally have one to three substituents selected from a halogen atom, a lower alkyl and a lower alkoxy" includes phenyl groups which may optionally have one to three substituents selected from a halogen atom, an alkyl having 1 to about 6 carbon atoms, for example, phenyl, 2-chlorophenyl, 3-chlorophenyl, 4-chlorophenyl, 2-bromophenyl, 3-bromophenyl, 4-bromophenyl, 4-fluorophenyl, 4-iodophenyl, 2,4-dibromophenyl, 2,6-dibromophenyl, 2,4,6-tribromophenyl, 2-methylphenyl, 3-methylphenyl, 4-methylphenyl, 2-ethylphenyl, 4-ethylphenyl, 3-propylphenyl, 4-(t-butyl)phenyl, 4-pentylphenyl, 4-heylphenyl, 2,4-dimethylphenyl, 2,6-dimethylphenyl, 2-methyl-4-ethylphenyl, 2,4,6-trimethylphenyl, 2-methoxyphenyl, 3-methoxyphenyl, 4-methoxyphenyl, 2-ethoxyphenyl, 4-ethoxylphenyl, 3-propoxyphenyl, 4-(t-butoxy)phenyl, 4-pentyloxyphenyl, 4-hexyloxyphenyl, 2,6-dimethoxyphenyl, 2-methoxy-4-ethoxyphenyl, 2,4,6-trimethoxyphenyl, 2-chloro-4-methylphenyl, 2,6-dibromo-4-methylphenyl, 2-chloro-4-methoxyphenyl, 2,6-dichloro-4-methoxylphenyl, 2-bromo-4-methoxyphenyl, 2,6-dibromo-4-methoxyphenyl, 2,6-dibromo-4-ethoxyphenyl, etc. The term "phenyl-lower alkyl" includes phenylalkyl groups having 1 to 6 carbon atoms in the alkyl moiety, for example, benzyl, 1-phenylethyl, 2-phenylethyl, 3-phenylpropyl, 2-phenyl-1-methylethyl, 4-phenylbutyl, 2-phenyl-1, 1-dimethylethyl, 5-phenylpentyl, 6-phenylhexyl, etc. The term "benzoyl which may optionally have one to three substituents selected from a halogen atom, a phenoyl-lower alkoxy and hydroxy on the phenyl ring" includes benzoyl groups which may optionally have one to three substituents selected from a halogen atom, a phenylalkoxy having 1 to about 6 carbon atoms in the alkoxy moiety and hydroxy, for example, benzoyl, 3-bromo-benzoyl, 4-benzyloxybenzoyl, 4-hydroxybenzoyl, 3,5-dibromobenzoyl, 3-bromo-4-benzyloxybenzoyl, 3-chloro-4-hydroxybenzoyl, 3,5-dibromo-4-benzyloxy-benzoyl, 3,5-dibromo-4-(1-phenethyloxy)benzoyl, 3,5-dibromo-4-(2-pheethyloxy)benzoyl, 3,5-dibromo-4-(3 -phenylpropoxy)benzoyl, 3,5-dibromo-4-(4-phenyl-butoxy)benzoyl, 3,5-dibromo-4-(5-phenylpentyloxy)-benzoyl, 3,5-dibromo-4-(6-phenylhexyloxybenzoyl, 3,5-dichloro-4-benzyloxybenzoyl, 3,5-dichloro-4-hydroxybenzoyl, 3,4-dichloro-5-hydroxybenzoyl, etc. The "term cycloalkyl" includes cycloalkyl groups having 3 to 8 carbon ring atoms, for example, cyclopropyl, cyclobutyl, cyclopentyl, cyclohexyl, cycloheptyl, cyclooctyl, etc. The term "furyl" includes, for example, 2-furyl, 3-furyl, etc. The term "thienyl" includes, for example, 2-thienyl, 3-thienyl, etc. The term "tetrahydrofuranyl" includes, for example, 2-tetrahydrofuranyl, 3-tetrahydrofuranyl, etc. The "hydroxy-substituted lower alkyl" includes hydroxy-substituted alkyl groups having 1 to about 6 carbon atoms in the alkyl moiety, for example, hydroxymethyl, I-hydroxyethyl, 2-hydroyethyl, 3-hydroxypropyl, 4-hydroxybutyl, 5-hydroxypentyl, 6-hydroxyhexyl, etc. The term "lower alkyl which may optionally have a substituent selected form hydroxy, furyl, thienyl, tetrahydrofuranyl and phenyl" includes alkyl groups having 1 to 6 carbon atoms which may optionally have a substituent selected from hydroxy, furyl, thienyl, tetrahydrofuranyl and phenyl, for example, 2-furfuryl, 3-furylmethyl, 1-(2-furyl)ethyl, 2-(3-furyl)ethyl, 3-2-furyl)propyl, 4-(3-furyl)butyl, 3-(2-furyl)pentyl, 6-(2-furyl)hexyl, 2-thienylmethyl, 3-thienylmethyl, 1-(2-thienyl)ethyl, 2-(3-thienyl)ethyl, 3-(2-thienyl)propyl, 4-(3-thienyl)butyl, 5-(2-thienyl)pentyl, 6-(2-thienyl)hexyl, 2-tetrahydrofuranylmethyl, 3-tetrahydrofuranylmethyl, 1-(2-tetrahydrofuranyl)ethyl, 2-(3-tetrahydrofuranyl)ethyl, 3-(2-tetrahydrofuranyl)propyl, 4-(3-tetrahydrofuranyl)-butyl, 5-(2-tetrahydrofuranyl)pentyl, 6-(2-tetrahydrofuranyl)hexyl, etc. The term "phenyl which may optionally have one to three substituents selected from a lower alkyl, a hydroxy-substituted lower alkyl, a lower alkanoyl, cyano, carboxy, a lower alkoxycarbonyl, hydroxy, a lower alkoxy, and a halogen atom" includes phenyl groups which may optionally have one to three substituents selected from an alkyl having 1 to 6 carbon atoms, a hydroxyalkyl having 1 to 6 carbon atoms, an alkanoyl having 1 to 6 carbon atoms, cyano, carboxy, an alkoxycarbonyl having 1 to 6 carbon atoms in the alkoxy moiety, hydroxy, an alkoxy having 1 to 6 carbon atoms, and a halogen, for example, phenyl, 2-methylphenyl, 3-methylphenyl, 4-methylphenyl, 2-ethylphenyl, 3-ethylphenyl, 4-ethylphenyl, 2-isopropylphenyl, 3-isopropylphenyl, 4-isopropylphenyl, 3-propylphenyl, 4-butylphenyl, 2-(t-butyl)phenyl, 3-(t-butyl)phenyl, 4-(t-butyl)phenyl, 4-pentylphenyl, 4-hexylphenyl, 4-hydroxymethylphenyl, 2-(1-hydroxyethyl)-phenyl, 3 -(1-hydroxyethyl)phenyl, 4-(1-hydroxyethyl)-phenyl, 2-(2-hydroxyethyl)phenyl, 4-(2-hydroxyethyl)-phenyl, 3-(3-hydroxypropyl)phenyl, 4-(4-hydroxybutyl)phenyl, 4-(5-hydroxypentyl)phenyl, 4-(6-hydroxyhexyl)phenyl, 2-acetylphenyl, 3-acetylphenyl, 4-acetylphenyl, 3-propionylphenyl, 4-butyrylphenyl, 3-valerylphenyl, 4-hexanoylphenyl, 2-cynaophenyl, 3-cyanophenyl, 4-cynaophenyl, 2-carbonxyphenyl, 3-carboxyphenyl, 4-carboxyphenyl, 2-methoxycarbonyl-phenyl, 3-methoxycarbonylphenyl, 4-methoxycarbonylphenyl, 2-ethoxycarbonylphenyl, 4-propoxycarbonylphenyl, 4-(t-butoxycarbonyl)phenyl, 4-pentyloxycarbonylphenyl, 4-hexyloxycarbonylphenyl, 2-hydroxyphenyl, 3-hydroxyphenyl, 4-hydroxyphenyl, 2-methoxyphenyl, 3-methoxyphenyl, 4-methoxyphenyl, 2,4-dimethoxyphenyl, 2,4,6-trimethoxyphenyl, 3,4,5-trimethoxyphenyl, 4-ethoxyphenyl, 4-t-butoxyphenyl, 4-hexyloxyphenyl, 2-chlorophenyl, 3-chlorophenyl, 4-chlorophenyl, 2,4,-dichlorophenyl, 3,5-dichlorophenyl, 2,4,6-trichlorophenyl, 3,4,5-trichlorophenyl, 4-bromophenyl, 4-fluorophenyl, 4-iodophenyl, 2-hydroxy-4-carboxyphenyl, 3-hydroxy-4-carboxyphenyl, 4-hydroxy-3-carboxyphenyl, 2-hydroxy-4-methoxycarbonylphenyl, 3-hydroxy-4-methoxycarbonylphenyl, 4-hydroxy-3-methoxycarbonylphenyl, 2-methoxy-4methoxycarbonylphenyl, 3-methoxy-4-methoxycarbonylphenyl, 4-methoxy-3-methoxycarbonlyphenyl, etc. The "heterocyclic group selected from pyridyl, pyrimidinyl, thiazolyl, isoxazolyl, and pyrazolyl, said heterocyclic group being optionally substituted by a lower alkyl, amino, or a lower alkanoy-lamino" includes heterocyclic groups selected from pyridyl, pyrimidinyl, thiazolyl, isoxazolyl, and pyrazolyl which may optionally substituted by an alkyl having 1 to about 6 carbon atoms, amino, or an alkanoylamino having 1 to about 6 carbon atoms in the alkanoyl moiety, for example, 2-pyridyl, 3-pyridyl, 4-pyridyl, 2-pyrimidinyl, 4-pyrimidinyl, 5-pyrimidnyl, 2-thiazolyl, 4-isoxazolyl, 1-pyrazolyl, 3-pyrazolyl, 4-pyrazolyl, 2-methyl-4-pyridyll, 4-methyl-3-pyridyl, 3-amino-5-pyridyl, 4-amino-2-pyridyl, 2-acetylamino-4-pyridyl, 3-propanoylamino-5-pyridyl, 2-methyl-4-pyrimidinyl, 4-methyl-6-pyrimidinyl, 5-ethyl-2-pyrimidinyl, 2-amino-5-pyrimidinyl, 2-amino-4-pyrimidiny, 4-acetylamino-2-pyrimidinyl, 4-acetylamino-6-pyrimidinyl, 4-propanoylamino-2-pyrimidinyl, 2-methyl-4-thiazolyl, 2-ethyl-5-thiazolyl, 4-methyl-2-thiazolyl, 2-amino-4-thiazolyl, 4-amino-5-thiazolyl, 2-acetylamino-4-thiazolyl, 5-acetylamino-2-thiazolyl, 5-methyl-3-isoxazolyl, 4-methyl-3-isoxazolyl, 4-methyl-5-isoxazolyl, 5-ethyl-3-isoxazolyl, 5-propyl-4-isoxazolyl, 4-isopropyl-3-isoxazolyl, 5-butyl-3-isoxazolyl, 5-pentyl-4-isoxazolyl, 5-heyl-3-isoxazolyl, 3-amino-4-isoxazolyl, 4-amino-5-isoxazolyl, 3-acetylamino-4-isoxazolyl, 5-acetylamino-3-isoxazolyl, 1-methyl-3-pyrazolyl, 3-methyl-5-pyrazolyl, 4-ethyl-1-pyrazolyl, 5-amino-1-pyrazolyl, 4-amino-1-pyrazolyl, 3-amino-1-pyrazolyl, 5-amino-3-pyrazolyl, 5-acetylamino-1-pyrazolyl, 4-acetylamino-1-pyrazolyl, 3-acetylamino-1-pyrazolyl, 5-acetylamino-3-pyrazolyl, 5-porpanoylamino-1-pyrazolyl, 4-butyrylamino-1-pyrazolyl, 5-isobutyrylamino-1-pyrazolyl, 5-valerylamino-1-pyrazolyl, 5-hexanoylamino-1-pyrazolyl, etc. The term "saturated 5- or 6-membered heterocyclic group which may optionally be intervened with oxygen atom formed by joining of $R^4$ and $R^5$ together with the adjacent nitrogen atom" includes, for example, pyrrollidinyl, piperidinyl, tetrahydro-1,2-oxazinyl, tetrahydro-1,3-oxazinyl, morpholino, etc. The term "lower alkylene" includes alkylene groups having 1 to 6 carbon atoms, for example methylene, ethylene, trimethylene, dimethylmethylene, tetramethylene, pentamethylene, hexamethylene, etc. The "group of the formula:

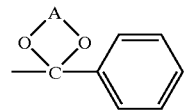

(wherein A is as defined above)" includes, for example, phenylmethylenedioxymethyl, phenylethylenedioxymethyl, phenylpropylenedioxymethyl, etc. Compounds of formula XXII can be suitably prepared by methods disclosed in U.S. Pat. No. 4,824,834.

Additional suitable triazine compounds for use in the methods of the invention include compounds of the following Formula XXIII:

XXIII

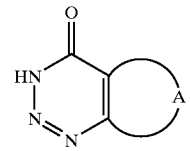

wherein A is a grouping of the formula

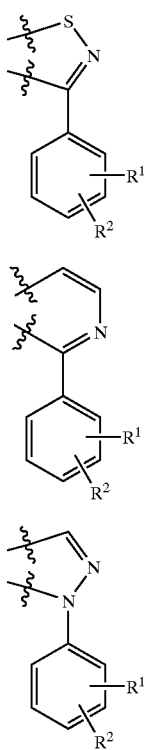

in which $R^1$ and $R^2$ each individually is hydrogen, halogen, trifluoromethyl, nitro, amino, cyano, $C_1$–$C_6$-alkyl, $C_1$–$C_6$-alkoxy, $C_3$–$C_6$-alkenyloxy, $C_1$–$C_6$-alkylthio, $C_1$–$C_6$-alkanoylamino, aryloxy, aryl-($C_1$–$C_6$-alkyl), aryl-($C_1$–$C_6$-alkoxy), aryl-($C_1$–$C_6$-alkoxy)carbonylamino or —O—CH$_2$—R$^3$, or $R^1$ and $R^2$ on adjacent carbon atoms together are —CH=CH—CH—CH=CH— or —CH$_2$—CH$_2$—O—, and $R^3$ is hydroxy-($C_1$–$C_4$-alkyl) or vicinal dihydroxy-($C_2$–$C_5$-alkyl), and pharmaceutically acceptable acid addition salts of those compounds of formula I in which at least one of $R^1$ and $R^2$ is amino, or tautomers thereof. As used in reference to Formula XXIII, the terms "$C_1$–$C_4$-alkyl", "$C_2$–$C_5$-alkyl" and "$C_1$–$C_6$-alkyl", mean straight-chain or branched-chain alkyl groups which contain the number of carbon atoms specified, such as methyl, ethyl, n-propyl, isopropyl, n-butyl, sec.butyl, tert.butyl, n-pentyl, n-hexyl and the like. The term "$C_1$–$C_6$-alkoxy" means a $C_1$–$C_6$-alkyl group as defined above which is attached via an oxygen atom, examples of $C_1$–$C_6$-alkoxy groups being methoxy, ethoxy, n-propoxy, isopropoxy, n-butoxy, isobutoxy, tert.butoxy and the like. The term "$C_3$–$C_6$-alkenyloxy" means a straight-chain or branched-chain alkenyloxy group containing from 3 to 6 carbon atoms such as allyloxy, butenyloxy and the like. The term "$C_1$–$C_6$-alkylthio" means a $C_1$–$C_6$-alkyl group as defined above which is attached via a sulfur atom, examples of $C_1$–$C_6$-alkylthio groups being methylthio, ethylthio, n-propylthio, isopropylthio, n-butylthio and the like. The $C_1$–$C_6$-alkanoyl residue of a $C_1$–$C_6$-alkanoylamino group is derived from a straight-chain or branched-chain alkanecarboxylic acid containing from 1 to 6 carbon atoms such as formyl acetyl, propionyl, butyryl and the like. The aryl moiety of an aryloxy, aryl-($C_1$–$C_6$-alkyl), aryl-($C_1$–$C_6$-alkoxy) or aryl-($C_1$–$C_6$-alkoxy)carbonylamino group is an unsubstituted phenyl group or a phenyl group carrying at least one substituent selected from halogen, trifluoromethyl, $C_1$–$C_6$-alkyl, $C_1$–$C_6$-alkoxy, nitro and cyano. Phenoxy, 4-chlorophenoxy, 4-tolyloxy etc are examples of aryloxy groups. Benzyl, 4-chlorobenzyl, 4-tolyl, 4-methoxybenzyl, phenethyl etc are examples of aryl ($C_1$–$C_6$alkyl) groups. Benzyloxy, 4-chlorobenzyloxy, 4-tolyloxy, 4-methoxybenzyloxy etc are examples of aryl-($C_1$–$C_6$alkoxy) groups. Examples of groups of the formula —O—CH$_2$—R$^3$ are 2-hydroxyethoxy, 3-hydroxypropoxy and the like when $R^3$ are 2-hydroxyethoxy, 3-hydroxypropoxy and the like when $R^3$ represents hydroxy-($C_1$–$C_4$-alkyl) and 2,3-dihydroxypropoxy, 3,4-dihydroxybutoxy and the like when $R^3$ represents vicinal dihydroxy-($C_2$–$C_5$-alkyl). The term "halogen" means fluorine, chlorine, bromine or iodine. The compounds of Formula XXIII in which $R^1$ and/or $R^2$ represents amino form pharmaceutically acceptable salts with acids. Examples of such salts are mineral acid salts such as hydrohalides (e.g. hydrochlorides, hydrobromides etc), sulphates, phosphates, nitrates etc and organic acid salts such as acetates, maleates, fumarates, tartrates, citrates, salicylates, methanesulphonates, p-toluenesulphonates etc.

It will be appreciated that the compounds of Formula XXIII can exist in tautomeric forms, and that such tautomers are within the scope of Formula XXIII.

A preferred group of compound of Formula XXIII above comprises those in which A represents a group of sub-formula (a) as specified above. In such compounds $R^1$ preferably represents hydrogen, halogen, trifluoromethyl or cyano and $R^2$ preferably represents hydrogen $C_1$–$C_6$-alkoxy, aryl-($C_1$–$C_6$-alkoxy) or a group of the formula —O—CH$_2$—R$^3$ in which $R^3$ represents vicinal dihydroxy-($C_2$–$C_5$-alkyl), with the proviso that at least one of $R^1$ and $R^2$ represents other than hydrogen. Particularly preferred compounds in which A represents a group of sub-formula (a) are 7-(3-trifluoromethyl-4-methoxyphenyl)isothiazolo[4,5-d]- 1,2,3-triazin-4(3H)-one; 7-(3-chloro-4-methoxyphenyl)isothiazolo[4,5-d]-1,2,3-triazin-4(3H)-one; 7-(3-fluoro-4-methoxyphenyl)isothiazolo[4,5-d]-1,2,3-triazin-4( 3H)-one; 7-(3-trifluoromethylphenyl)isothiazolo[4,5-d]-1,2,3-triazin-4(3H )-one; 7-(4-isopropoxyphenyl)isothiazolo[4,5]d]-1,2,3-triazin-4(3H)-one; 7-(4-benzyloxyphenyl)isothiazolo[4,5-d]-1,2,3-triazin-4(3H)-one; 7-(3-cyano-4-methoxyphenyl)isothiazolo[4,5-d]-1,2,3-triazin-4(3H)-one; and 7-[3-cyano-4-(2,3-dihydroxypropoxy)phenyl)isothiazolo[4,5-d]-1,2,3-triazin-4(3H)-ene.

Another preferred group of compounds of Formula XXIII comprises those in which A represents a group of sub-formula (c) as specified above. In such compounds R preferably represents hydrogen and $R^2$ preferably represents $C_1$–$C_6$-alkoxy.

Compounds of Formula XXIII can be suitably prepared as disclosed in U.S. Pat. No. 4,920,119.

Additional compounds suitable for use in the methods of the invention are also disclosed in the following published patents and patent applications:

European 429,038, particularly the disclosed phenylethenyl esters of phenyl-propenoic acid;

PCT Publication 9113623, particularly the disclosed C5-monosubstituted barbiturates;

Czechoslovakia 264505, particularly the disclosed salts of N-acetyl-p-aminosalicylic acid;

German 3912092, particularly the disclosed heterocyclic compounds with more than one hetero atom, such as amino-triazolopyridoquinazolinone;

Japanese 02245198, particularly the disclosed phenol compounds such as sodium salicylate;

European 269859, particularly the disclosed pyrazolotriazines;

European 274654, particularly the disclosed heterocylotriazinones such as 7-phenylisothiazolo [4,5-d]-1,2,3-triazin-4(3H)-one;

Netherlands 8602382, particularly the disclosed catechol derivatives such as 4-(+)-methylthiocatechol);

German 3632841 particularly the disclosed catechol derivatives;

German 3632824, particularly the disclosed bicyclic catechol derivatives;

Japanese 59219229, particularly the disclosed indoles, such as 1-formyl-4-hydroy-9H-pyridol[3,4-b]indole;

U.S. Pat. No. 4,336,257, particularly the disclosed 2-(4-pyridyl)-5-chlorobenzimidazole, 1H-imidazo[4,5-b]pyridines, and imidazo[4,5-c]pyridines;

European 28660, particularly the disclosed pyrazolobenzotriazine derivatives;

Japanese 55055185, particularly the disclosed compounds derived from extraction of picrasma quassioides;

German 2941449, particularly the disclosed pyridolindoles isolated according to the above patent;

U.S. Pat. No. 4,110,456, particularly the disclosed imidazoles, including sulfamoylimidazoles;

U.S. Pat. No. 4,032,522, particularly the disclosed trifluoromethylimidazoles;

U.S. Pat. No. 3,988,324, particularly the disclosed heterocyclobenzothiadiazinesulfonamides;

Japanese 51054576, particularly the disclosed hydroxy or acyloxyalkylaminobenzothiadiazines;

U.S. Pat. No. 3,960,854, particularly the disclosed 7-mercapto (or thio) benzothiadiazine-1,1 -dioides;

U.S. Pat. No. 3,969,518, particularly the disclosed 3-haloalkyl benzothiadiazine- 1,1 -dioxides;

U.S. Pat. No. 3,951,966, particularly the disclosed heterocycle-substituted benzothiodiazines;

Japanese 51006992, particularly the disclosed dihydrothiazoloadenines;

Japanese 51006993, particularly the disclosed midazoaoadenines and pyrimidnoadenines;

French 2262977, particularly the disclosed formylaminoallylidenehydrazines, substituted with aryl groups;

French 2262976, particularly the disclosed formamidrazones, substituted with aryl groups;

German 2410650, particularly the disclosed formamidrazones, isonicotinyl pyrimidinones and the like;

German 2410579, particularly the disclosed orotic acid hydrazide, and the corresponding nicotinic and isonicotinic acid derivative;

German 2509130, particularly the disclosed acryloylformamidrazones, pyrimidinones and the like;

German 2410653, particularly the disclosed acylpyrazolocarboxamides;

German 2508934, particularly the disclosed formylcarbamoylpyrazoles substituted with heterocyclic and carbocyclic aryl groups;

German 2410611, particularly the disclosed nicotinic acid hydrazide, azapentadienylidene;

German 2509094, particularly the disclosed aminoazapentadienylidene hydrazine;

German 2509049, particularly the disclosed morpholinoacryloylgormamidrazones substituted with various aryl groups;

German 2509175, particularly the disclosed substituted 2-hydrazonomethyl-3-hydroxy-4-aza-2,4-pentadienenitriles;

German 2410614, particularly the disclosed heterocyclic N-acyl-N'-(3-amino-2-cyanoacryloy) formamidrazones;

Japanese 50004039, particularly the disclosed salicylanilides;

British 1403974, particularly the disclosed dioxo-6,6-azopurine;

Japanese 49072298, particularly the disclosed 9-substituted palmatine derivatives;

German 2457127, particularly the disclosed haloimidazoles substituted with pyridyl and the like;

Japanese 49127943, particularly the disclosed 4-(2-hydroxybenzamido)salicylic acids;

German 2418467, particularly the disclosed hydroxybenzanilides;

Japanese 49048664, particularly the disclosed hydroxyalkyl imidazoles;

U.S. Pat. No. 3,816,625, particularly the disclosed 7-alkylsulfonyl-substituted benzothiadiazine-dioxides;

U.S. Pat No. 3,816,626, particularly the disclosed 3-pyridyl-1,2,4-benzothiadiazine-1,1-dioxides;

U.S. Pat. No. 3,816,631, particularly the disclosed 6-sulfamoyl-7-substituted-(3H)quinazolinones;

German 2356690, particularly the disclosed pyrazolo[3,4-d]pyrimidine N-oxides;

German 2344767, particularly the disclosed 2-cyanopyrimidine-4(1H)ones;

German 2351126, particularly the disclosed 6-sulfamoyl-4(3H)quinazolinones;

German 2343702, particularly the disclosed 4-mercapto-1H-pyrazolo[3,4d]pyrimidine;

German 2344733, particularly the disclosed 3-chloro-2-(hydrazonomethyl)-4-aza-2,4-pentadienenitriles;

German 2344738, particularly the disclosed 2-hydrazonomethyl-3-hydroxy-4-aza-2,4-pentadienenitriles;

German 2224379, particularly the disclosed 7-βD-ribofuranosyl-4,6-dihydroxypyrazolo[3,4-d]pyrimidine;

German 2318784, particularly the disclosed N-(2,4-dihydroxybenzoyl)-4aminosalicylic acids;

Japanese 48067491, particularly the disclosed formyluracils;

German 2313573, 7-mercapto-1,2,4benzothiadiazine 1,1-dioxide;

German 2313636, particularly the disclosed benzothiadiazines substituted with heterocyclic groups;

German 1966640, particularly the disclosed 4-hydroxypyrazolo[3,4-d]pyrimidines;

French 214377, particularly the disclosed 3-(2-chlorobenzoylamino)benzoic acid derivatives;

German 2255247, particularly the disclosed 5-(5-indanyloxy)tetrazoles;

German 2236987, particularly the disclosed pyrazolo[1,5-a]pyrimidines;

French 2109005, particularly the disclosed 4-(2-quinoxalinyl)phenoxyacetic acid derivatives;

French 2081360, particularly the disclosed 2,5-disubstituted imidazoles;

German 2147794, particularly the disclosed 1,2,4-triazoles substituted with heterocyclic and other aryl groups;

German 1927136, particularly the disclosed 1-D-ribosylallopurinol;

French 4777, particularly the disclosed 4-mercaptopyrazolo[3,4-d]pyrimidine; and French 1480652, particularly the disclosed 4-oxo-5-alkylpyrazolo[3,4-pyrimidines.

As discussed above, suitable therapeutic compounds for use in the methods of the invention can be synthesized by known procedures, including by procedures described in the above-cited documents. Some therapeutic compounds also are commercially available, such as allopurinol and oxypurinol.

As also discussed above, typical subjects for administration in accordance with the invention are mammals, such as primates, especially humans. For veterinary applications, a wide variety of subjects will be suitable, e.g. livestock such as cattle, sheep and the like; and domesticated animals, particularly pets such as dogs and cats.

Allopurinol has several theoretical advantages over currently available $Ca^{2+}$ sensitizers. Current $Ca^{2+}$ sensitizers shift the range of $Ca^{2+}$ activation so that force is activated at lower levels of $Ca^{2+}$ with a consequent risk for diastolic dysfunction. Additionally, most of the currently available $Ca^{2+}$ have phosphodiesterase inhibitor activity. The advantages of in vivo use of XO inhibitors, specifically allopurinol are first, allopurinol has no adverse effect on diastolic function. Second. allopurinol acted only in dogs with heart failure and therefor did not adversely affect healthy dogs. Third, it is well established that allopurinol exhibits no phosphodiesterase inhibition thereby decreasing the occurrence of side-effects associated with such inhibition. As shown in examples 5-, allopurinol can act as a novel inotropic agent which simultaneously decreases oxygen consumption and markedly increase myocardial mechanical efficiency in the canine heart in vivo.

In the therapeutic methods of the invention, a subject such as a mammal is suitably selected that is need of treatment, e.g. a subject that is suffering from heart failure including congestive heart failure and cardiogenic shock, and then administering to such selected subject a therapeutic compound in accordance with the invention.

Compounds of the invention are suitably administered to a subject in a protonated and water-soluble form, e.g., as a pharmaceutically acceptable salt of an organic or inorganic acid, e.g., hydrochloride, sulfate, hemi-sulfate, phosphate, nitrate, acetate, oxalate, citrate, maleate, mesylate, etc. Also, where an acidic group is present on a therapeutic compound, a pharmaceutically acceptable salt of an organic or inorganic base can be employed such as an ammonium salt, or salt of an organic amine, or a salt of an alkali metal or alkaline earth metal such as a potassium, calcium or sodium salt. Specifically suitable pharmaceutically acceptable salts also have been disclosed above.

In the methods of the invention, a therapeutic compound such as a xanthine oxidase inhibitor compound may be administered to a subject by a variety of routes including parenteral (including intravenous, subcutaneous, intramuscular and intradermal), topical (including buccal, sublingual), oral, nasal and the like.

Therapeutic compounds for use in the methods of the invention can be employed, either alone or in combination with one or more other therapeutic agents, as a pharmaceutical composition in mixture with conventional excipient, i.e., pharmaceutically acceptable organic or inorganic carrier substances suitable for a desired route of administration which do not deleteriously react with the active compounds and are not deleterious to the recipient thereof. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds.

For parenteral application, particularly suitable are solutions, preferably oily or aqueous solutions as well as suspensions, emulsions, or implants, including suppositories. Ampules are convenient unit dosages.

For enteral application, particularly suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc. Tablets, capsules and syrups or other fluids are generally preferred for oral administration.

A single or combination of more than one distinct therapeutic compound may be administered in a particular therapy. In this regard, a particular therapy can be optimized by selection of an optimal therapeutic compound, particularly optimal xanthine oxidase inhibitor compound, or optimal "cocktail" of multiple xanthine oxidase inhibitor compounds. Such optimal compound(s) can be readily identified by those skilled in the art, such as by the in vitro and in vivo assays of the examples which follow.

Also, as mentioned above, other pharmaceutical agents may be administered in coordination with administration of a therapeutic compound of the invention, particularly a xanthine oxidase inhibitor. For example, an ACE-inhibitor such as captopril or enalapril may be administered with a xanthine oxidase inhibitor, e.g. separately or substantially simultaneously such as by formulating the two agents as a unitary pharmaceutical composition for administration to a patient.

It will be appreciated that the actual preferred amounts of active compounds used in a given therapy will vary according to the specific compound being utilized, the particular compositions formulated, the mode of application, the particular site of administration, etc. Optimal administration rates for a given protocol of administration can be readily ascertained by those skilled in the art using conventional dosage determination tests conducted with regard to the foregoing guidelines. At least some therapeutic compounds such as allopurinol have been previously used clinically and thus safety of such compounds is established. Also, doses employed in such prior clinical applications will be provide further guidelines for preferred dosage amounts for methods of the present invention.

All documents mentioned herein are incorporated herein by reference.

The following non-limiting examples are illustrative of the invention.

EXAMPLE 1

Thin specimens of rat cardiac muscle were dissected, mounted in a tissue bath for the measurement of contractile force, and microinjected with fura-2 to enable measurement of intracellular calcium concentration ($[Ca^{2+}]_i$). Procedures of this assay are disclosed in Gao, W. D. et al., *Circulation Research* 1995, 76(6):1036–1048. FIG. 1 of the drawings shows the effects of exposure to allopurinol. As shown in FIG. 1, allopurinol increases contractile force, while decreasing calcium ion concentration. This is the hallmark of a calcium-sensitizing effect.

EXAMPLE 2

Figure 2:
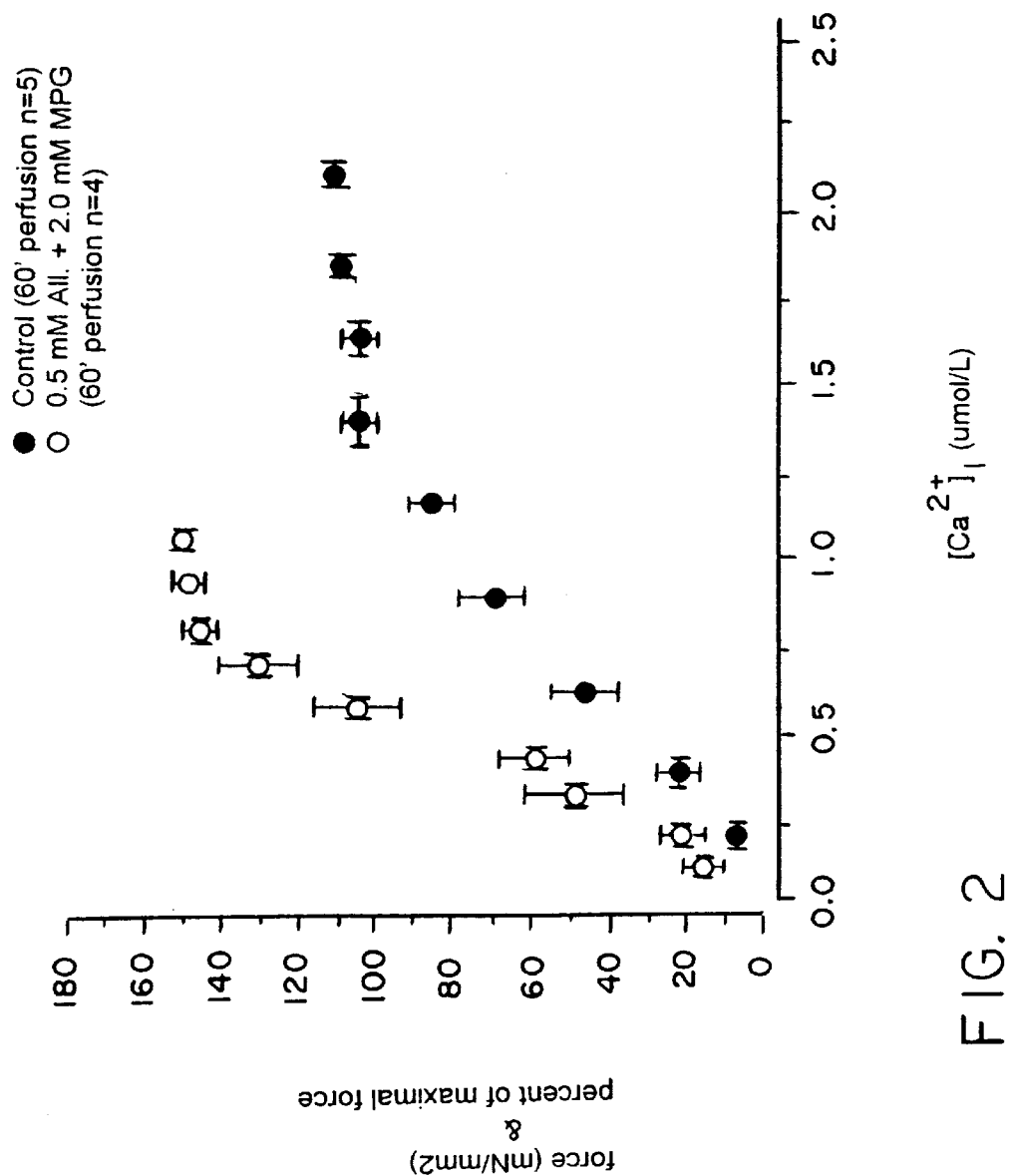
FIG. 2 shows graphically the results of Example 2, specifically the effects on the steady state contractile force of cardiac muscle upon exposure to allopurinol (open circles in plot) and a control of no drug (closed circles in plot).

A particularly rigorous method of assessing calcium sensitivity is by steady-state analysis by procedures disclosed in Gao, W. D. et al., supra. FIG. 2 of the drawings shows a plot of steady-state force versus steady-state $[Ca^{2+}]_i$ in control muscles (exposed to no drug; filled circles) and in muscles exposed to allopurinol (open circles). Allopurinol shifted the contractile activation curve to lower $[Ca^{2+}]_i$ and increased maximal force. That response represents defining characteristics of a calcium-sensitizing agent.

EXAMPLE 3

Figure 3:
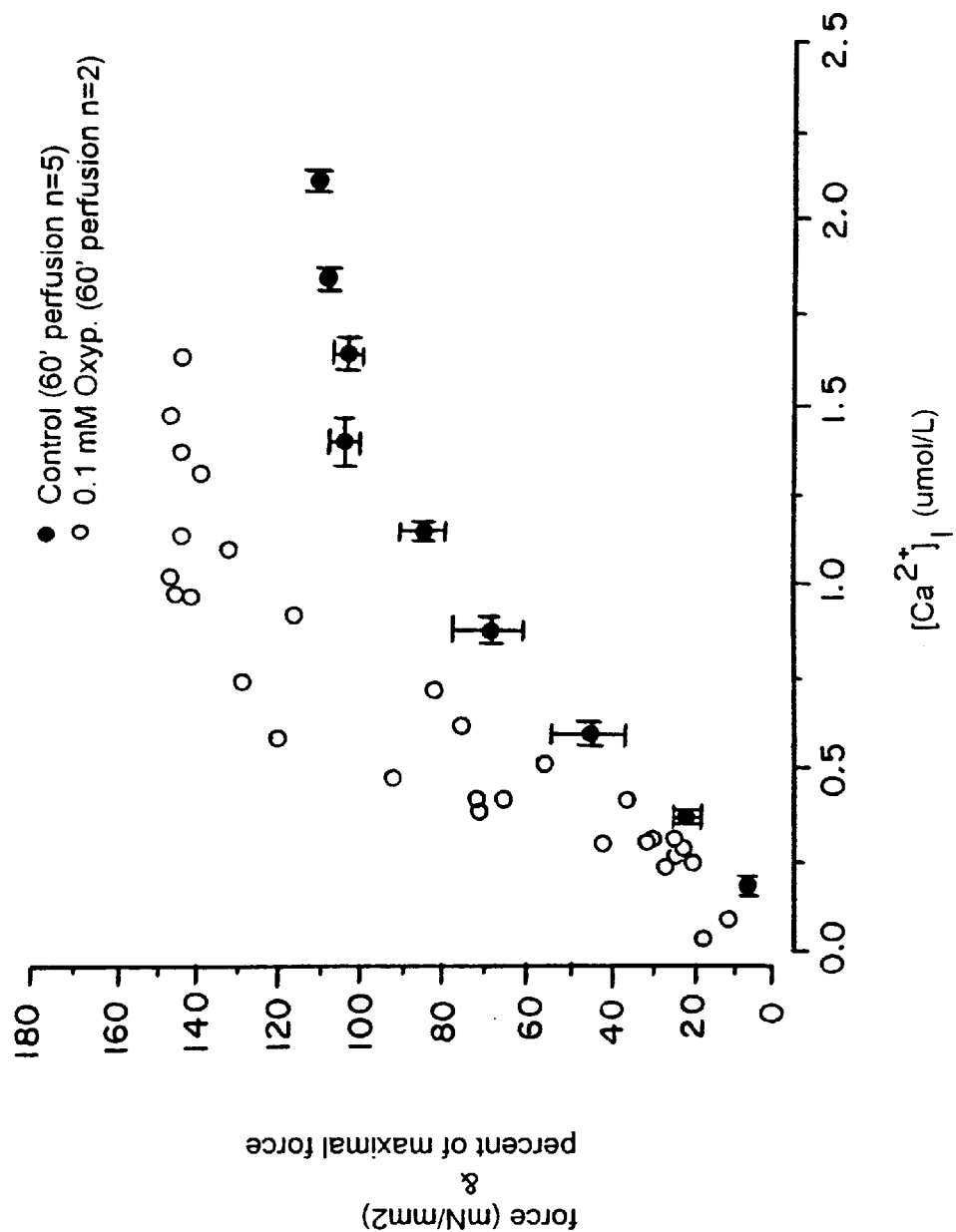
FIG. 3 shows graphically the results of Example 3 which follows, specifically effects on the steady state contractile force of cardiac muscle upon exposure to oxypurinol (open circles in plot) and a control of no drug (closed circles in plot).
Figure 4:
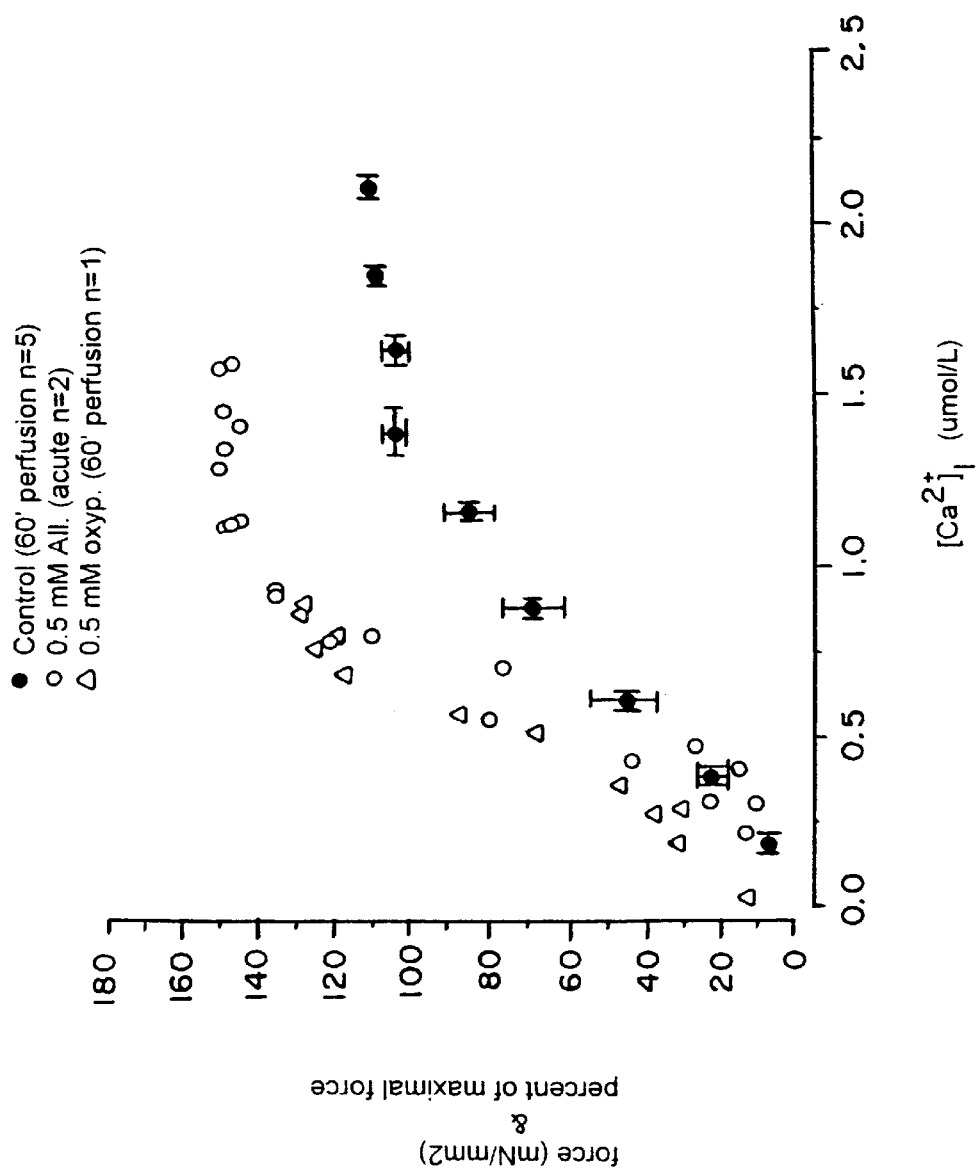
FIG. 4 shows graphically the results of Example 3 which follows, specifically the effects on the steady state contractile force of cardiac muscle upon exposure to allopurinol (open circles in plot), oxypurinol (open circles in plot) and a control of no drug (closed circles in plot).

FIG. 3 of the drawings shows that oxypurinol-treated muscles (open circles) generate more force at any given $[Ca^{2+}]_i$ than control muscles (filled circles). FIG. 4 compares the effects of allopurinol (open circles) and oxypurinol (triangles); the two agents have essentially indistinguishable effects on calcium sensitivity.

General comments for Examples 4–6.

In Examples 4–6 below, the following materials and methods were employed.

1. Surgical preparation for chronic dog protocol. Male mongrel dogs (20–30 kg) were anesthetized with 1–2% halothane after induction with sodium pentothal. The chest was opened via a lateral thoracotomy, and indwelling catheters (Tygon; Norton Plastics and Synthetic Division) were secured in the right atrium (for drug infusion) and in the descending aorta (for pressure measurement). An indwelling high fidelity micromanometer (P22, Konigsberg Instruments) was placed in the left ventricle (LV) through an apical stab. Endocardial sonomicrometer crystals were inserted for the measurement of anterior-posterior short axis dimension, and a pneumatic occluder was placed around the inferior vena cava (IVC) to allow preload reduction in order to assess LV pressure-dimension relations. Pacing leads were attached to the left atrium for acute pacing during experimentation, and epicardial leads for chronic pacing were attached to the right ventricular free wall and connected to a programmable pacemaker (Spectrax, Medtronics) within a subcutaneous pocket. The chest was closed in layers, catheters and leads were externalized to the mid-scapulae, and protected by an external jacket. Analgesia (morphine, 10 mg s.c.) was given in the immediate postoperative period as necessary. Antibiotics were administered for the first 72 hours after surgery. The dogs were allowed to recover fully for 7–10 postoperative days before experimentation. The surgical and experimental protocol was approved by Johns Hopkins School of Medicine Animal Care and Use Committee.

2. Drugs Preparation. 200 mg allopurinol (Sigma) was dissolved in 100 ml normal saline after slight heating and alkalization with NaOH. Control experiments demonstrated that the vehicle itself had no effect on cardiac or systemic hemodynamics and did not change arterial acid base balance.

3. Heart failure was induced by chronic rapid ventricular pacing at a rate of 210 bpm for 3 weeks, followed by 240 bpm for one week. This brought the dogs into heart failure with an average left ventricular end-diastolic pressure (LVEDP) of 23.5∀5.2 mm Hg. Acute pacing (140 bpm) was used to keep heart rate constant during the experiments.

4. Methods of Hemodynamic and Energetic Data Analysis a. The analysis of pressure-dimension relationships and the arterial pressure response allowed the evaluation of variables related to myocardial systolic and diastolic performance. Averaged data from 10–20 consecutive beats were used to derive steady-state parameters, and data measured during transient unloading of the heart by occlusion of the inferior vena cava (IVC) was used to assess pressure-dimension or pressure-volume relations. Preload was indexed as the left ventricular end diastolic anterior-posterior short axis dimension (LVEDD) or the LV end-diastolic volume from the conductance catheter. Afterload was evaluated as effective arterial elastance (Ea, ratio of LV systolic pressure to stroke dimension (Kass, D. A. 1997, Myocardial Mechanics. In Heart Failure. P. Poole-Wilson et al., eds. Churchill Livingstone, New York. 87–108; Kelly, R. P., C. T. Ting, and T. M. Yang. 1992, *Circulation* 86:513–521). This parameter is not preload-dependent and has been validated to reflect total afterload, which incorporates systemic vascular resistance, aortic impedance, and the reflected wave properties of the vasculature. Contractility was indexed by +dP/dt and the load-independent parameter, preload-recruitable stroke work (PRSW; slope of stoke work/end-diastolic dimension relation) (Kass, D. A., 1986, *Circulation* 73:586–595). Diastolic performance was measured by peak −dP/dt, time to peak filling rate (ttpf), and the time constant of relaxation (tau). Tau was calculated using the method of Weiss and colleagues (Ingwall, J. S. 1993, *Circulation* 87:VII-58–VII-62.).

b. Oxygen consumption per unit time ($MVO_2$) in the left circumflex artery territory was calculated from the difference in oxygen saturation in simultaneously sampled coronary sinus and aortic blood, multiplied by left circumflex coronary blood flow. This, in turn, was calculated from flow velocity multiplied by left circumflex diameter. Left circumflex diameter was analyzed from a film projector (CAP 35B, Angiogram Projection System) using quantitative angiography (Cath View v1.36, Image Comm Systems).

c. The external useful work of the LV was indexed as stroke work (SW=area of pressure-volume loops). Both stroke SW and $MVO_2$ were converted to Joules per beat (Suga, H. et al. 1983, *Circ. Res.* 53:306–318). Cardiac mechanical efficiency was calculated as $SW/MVO_2$. Hemodynamic pressure-dimension data were digitized at 200 Hz and stored for subsequent analysis on a personal computer using customized software.

d. All results are reported as mean ∀ SEM. Baseline hemodynamic variables before and after the 4-week pacing protocol were compared using Student's t-test or Kruskal-Wallis test, as appropriate.

Concentration-effect relationships were analyzed with a two-way ANOVA using a term for individual experiment. To analyze shifts in slope or position of the PRSW relation (stroke work vs. end-diastolic dimension) we compared SW-dimension data by multiple linear regression with an interaction term for drug effect. For comparisons between normal and heart failure dogs we used a two-tailed Student's t-test. All statistical analyses were performed using SYSTAT of SAS software. Differences were considered significant at P-values <0.05.

EXAMPLE 4

In Vivo Evaluation in Canine Heart Muscle

To test the effects of allopurinol on cardiac performance in the conscious state, data were collected with the dog standing quietly in a sling. Allopurinol (200 mg) was infused into the right atrium at a rate of 3.3 mL/min. The dose of allopurinol was extrapolated from the plasma levels achieved in humans (3–9 mg/L) after a standard dose (300 mg p.o.) of allopurinol (P.A. Insel Analagestic-antipyretic and anti-inflammatory agents, The Pharmacological Basis of Therapeutics (McGraw Hill, NY 1998)). In our 25 kg dogs, using the plasma half-life of 1.5 h and a distribution volume of 1.6 L/kg, a comparable plasma level (4.5 mg/L) was estimated to be attained by 200 mg allopurinol i.v. Pressure-dimension relationships and the arterial pressure response were recorded in the steady state and during IVC occlusion at baseline, every 10 min during infusion, and 10 and 20 min after cessation of the infusion. The ECG was continuously monitored.

Experiments to analyze the response to allopurinol in cardiac energetics were performed under isoflurane anesthesia (1.5–2.5%), after induction with sodium pentothal (25 mg/kg), in normal and heart failure dogs using acute instrumentation. Isoflurane was chosen as the anesthetic because of its relatively mild and stable effect on the cardiovascular system (R M. Jones, *British Journal of Anaesthesia*, 56 Suppl 1:57S–69S (1984); E. I. Eger, *British Journal of Anaesthesia*, 56 Suppl 1:71S–99S (1984)). A doppler flow velocimeter (0.014 Cardiometrics) and a 6 Fr. angiography catheter (AL-I or JL 3.5, Cordis Laboratories Inc) were inserted through an 8 Fr sheath (Cordis) in the right femoral artery and advanced to the left circumflex coronary artery. These catheters permitted measurement of coronary flow and injection of contrast for the measurement of coronary diameter. A catheter (A2 multipurpose, 6 Fr.) was advanced from the left external jugular vein via a 7 Fr. sheath (Cordis) into the great cardiac vein for withdrawal of mixed coronary venous blood. To measure cardiac oxygen consumption, blood samples from the coronary sinus and the femoral artery were obtained simultaneously. At each time point, blood flow velocity in the left circumflex artery was measured and coronary angiography was performed.

In 4 of 11 experiments, preexisting indwelling sonomicrometer crystals, Konigsberg micromanometers, and IVC occluders (see above) were used for dimension and pressure measurements, and for acute preload reduction. In the other 7 experiments, a combined micromanometer-conductance catheter (M!illar) was advanced to the LV and positioned for continuous measurement of LV pressure and volume via a 7 Fr. sheath (Cordis) in the femoral artery. A Swan-Ganz catheter (Arrow, 7 Fr.) was advanced via a 9F sheath in the femoral vein to the pulmonary artery for measurement of cardiac output and for hypertonic saline wash-in (Baan, J., E. van der Velde, A. D. van Dijk and et al. 1992, In Cardiovascular system dynamics: Models and measurements. Anonymous Plenum Press, New York, 569; Kass, D. A. et al. 1986. *Circulation* 73:586–595) to calibrate the volume signal. This catheter was then replaced with a balloon occlusion catheter (Cordis) positioned in the IVC for acute preload reduction for pressure-volume analysis.

Figure 5:
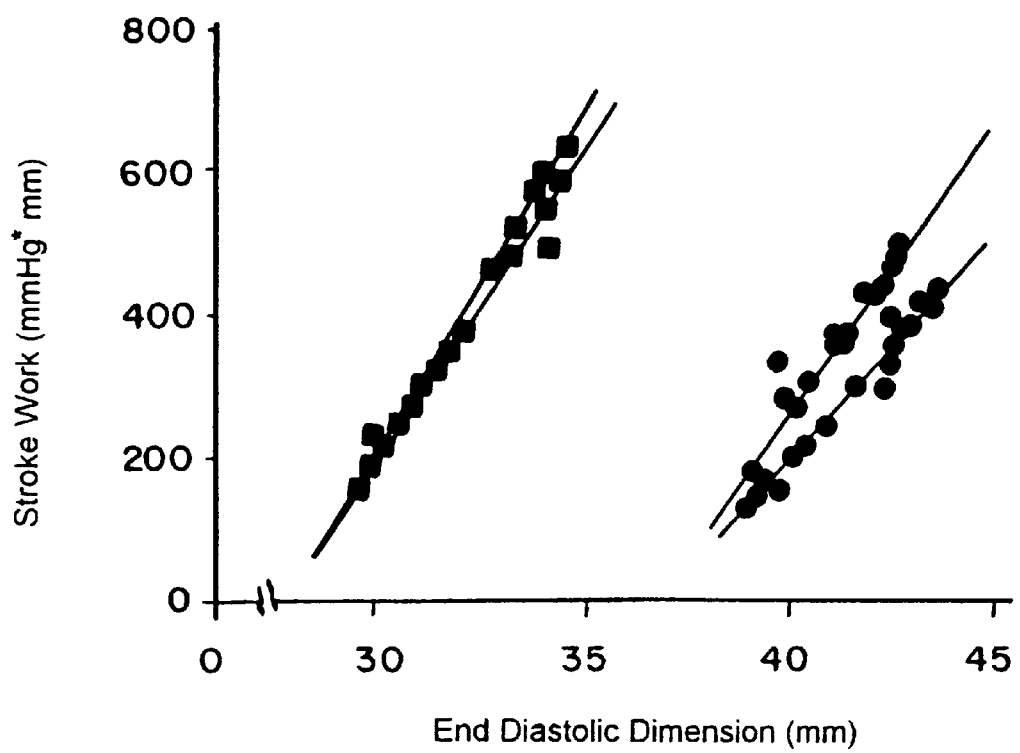

Results are shown in FIGS. 5–8 of the drawings. FIG. 5 shows the effect of allopurinol on the relation between stroke work and end-diastolic dimension. 200 mg allopurinol was infused in 100 mL NS over 30 minutes in the right atrium of dogs chronically instrumented to measure LV pressure and dimension at baseline and after pacing-induced heart failure. Depicted are PRSW relationships obtained by a transient occlusion of the inferior vena cava at baseline and after allopurinol. Note the lack of inotropic effect in controls and positive inotropy in heart failure dogs. The agent did not affect the slope of the PRSW relation I the control state but increased the slope after heart failure indicating a positive inotropic effect.

Figure 6B:
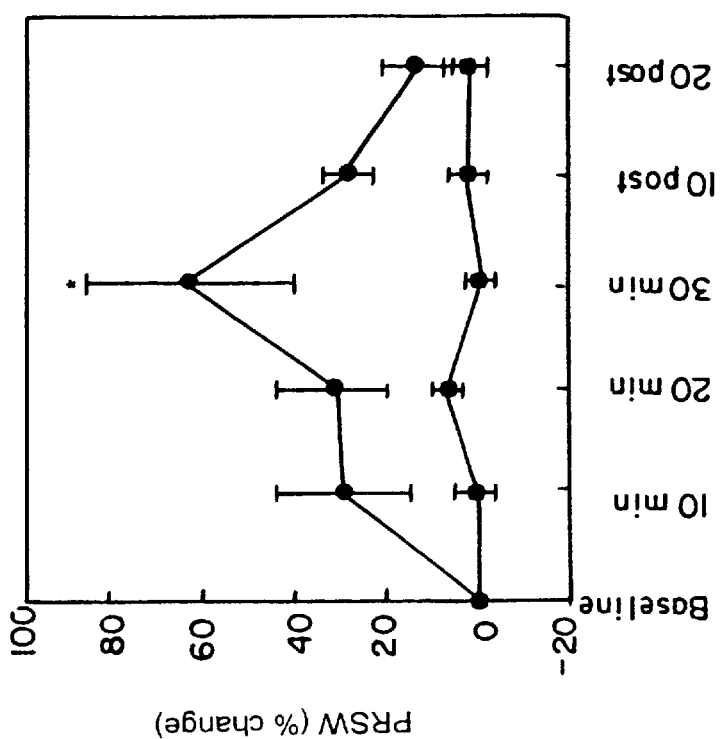
FIGS. 6A–6B show graphically the results of Example 4 which follows, specifically the effect of allopurinol on myocardial contractility in conscious dogs.
Figure 6A:
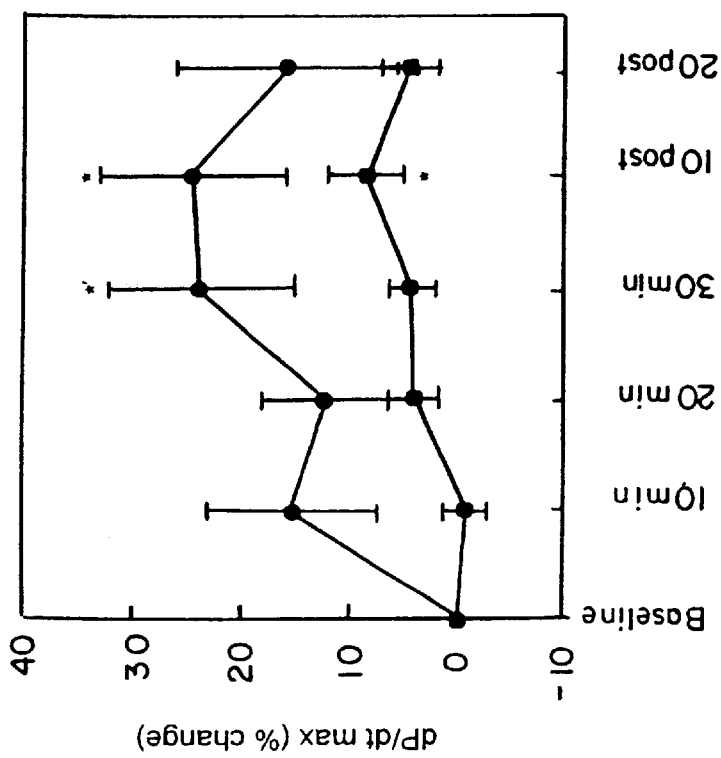

FIG. 6 shows the time course of the allopurinol-induced changes in LV contractility in conscious dogs before and after pacing-induced heart failure. In control dogs (n=10), allopurinol increased $(dP/dt)_{max}$ (FIG. 7A) from a base line value of 3101±162 to 3373±225 mm Hg/s (+8.3±3.2%, p=0.01) at the peak response, which occurred 10 min after the end of the infusion. The positive inotropic effects of allopurinol persisted, and in some cases continued to rise, for some time after the infusion, with values not completely returning to baseline during a 20 min observation period. However, PRSW (FIG. 6B) was not significantly changed.

Figure 7B:
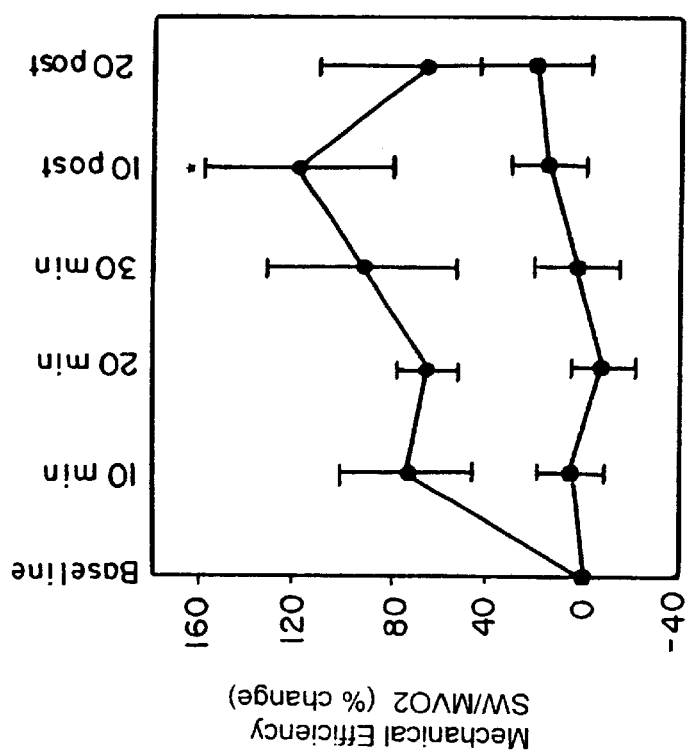
FIGS. 7A–7B show graphically the results of Example 4 which follows, specifically the effect of allopurinol on $O_2$ consumption and mechanical efficiency anesthetized control and heart failure dogs.
Figure 7A:
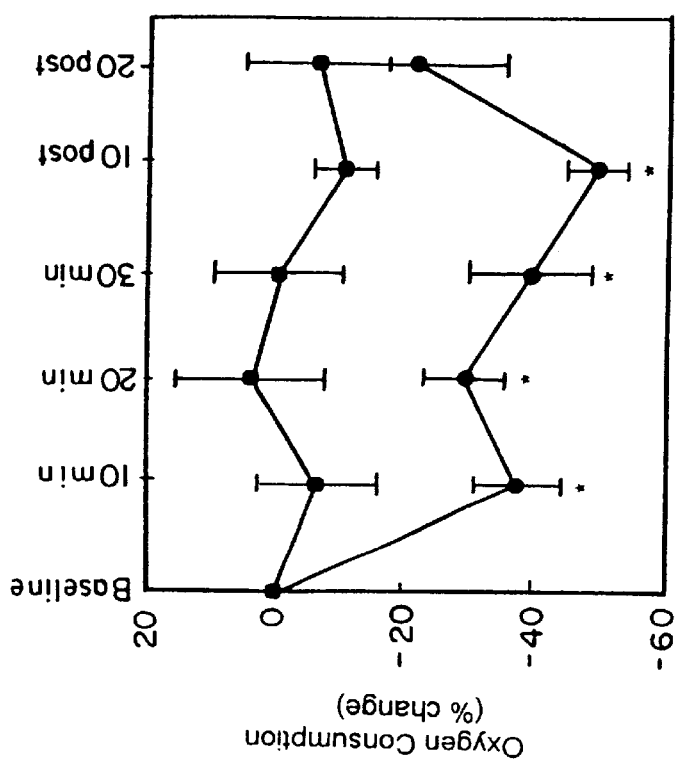

FIG. 7 shows the effects of allopurinol on $O_2$ consumption and mechanical efficiency in anesthetized control and heart failure dogs. A combined manometer-conductance catheter was positioned in the left ventricle for continuous measurement of volume and pressures in the ventricle for continuous measurement of volume and pressures in the ventricle and aorta. Volume was calibrated with measurement of cardiac output and hypertonic saline wash-in. In addition, dogs were acutely instrumented a doppler flow velocimeter probe and an angiography catheter in the left circumflex coronary artery to measure coronary flow velocity and coronary diameter. A catheter was placed in the great cardiac vein for withdrawal of mixed coronary venous blood simultaneously with arterial blood samples to calculation of cardiac oxygen extraction. Depicted are effects of allopurinol on $O_2$ consumption (panel a) and mechanical efficiency ($SW/O_2$ consumption; panel b) in the circumflex territory of normal (n=5) and failing (n=6) dog hearts.

Figure 8:
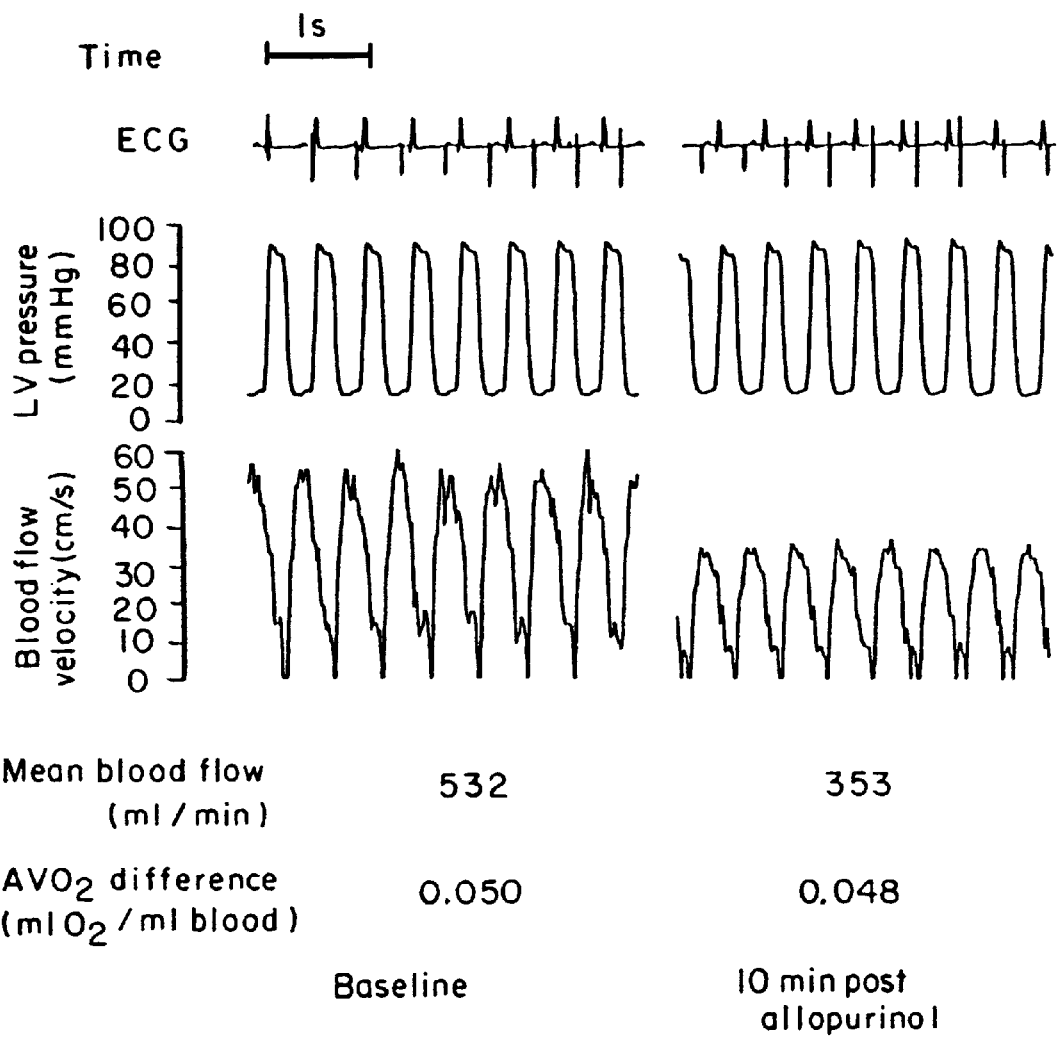

FIG. 8 depicts an original tracing of left circumflex blood flow velocity during allopurinol infusion. Panel a shows blood flow velocity before and 10 min after 200 mg allopurinol iv over 30 minutes in a heart failure dog. Panel b shows compiled data for blood flow and arterio-venous oxygen difference (panel c) from 5 control and 6 heart failure dogs. Note blood flow decrease, while coronary oxygen extraction is unchanged, in response to allopurinol in heart failure. The decrease in oxygen consumption was manifested primarily as a decrease in left circumflex blood flow (−40±6 % 10 min post-infusion , p=0.0015), whereas myocardial arterio-venous oxygen difference was not changed. These results indicate that allopurinol decreases oxygen utilization and increases mechanical efficiency in the failing canine left ventricle.

EXAMPLE 5

Comparison of Energetic Effects of Allopurinol to Those of Dobutamine

Figure 9:
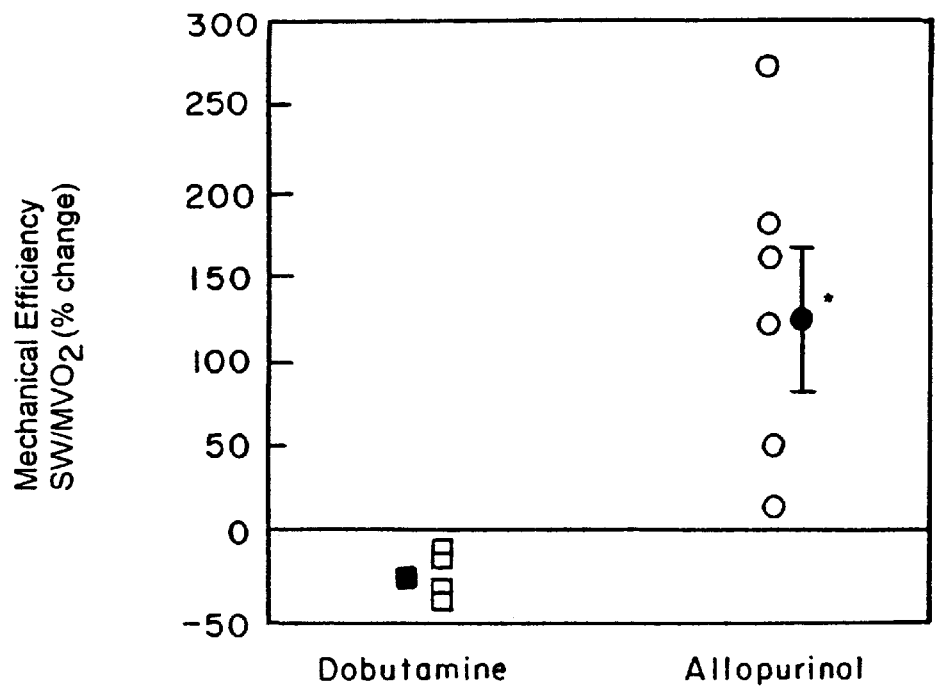
FIG. 9 shows graphically the results of Example 5 which follows, specifically the comparison of energetic effects of allopurinol to those of dobutamine.

In 5 of the 6 dogs undergoing assessment of energetics after heart failure, dobutamine 10 μg/Kg/min was also infused. This was performed to compare the energetic consequences (oxygen cost for increasing myocardial contractility) between allopurinol and a β-adrenergic agonist. This study was performed on a separate day. In contrast to allopurinol, as shown in FIG. 9, dobutamine caused a significant decrease in mechanical efficiency. Following infusion of dobutamine, oxygen consumption increased by 145±53.0 % (p=0.007) and $SW/MVO_2$ decreased −29.3±6.8%(p=0.05).

EXAMPLE 6

Method of Evaluating Xanthine Oxidase Activity in Myocardium Obtained from Control and Heart Failure Dogs Myocardial tissue samples were obtained from additional animals, dogs, (n=13) immediately after sacrifice using intravenous KCl. The analysis was also performed in 2 dogs that received allopurinol on the same day. Samples were immediately frozen in liquid nitrogen and stored a −80° C. for analysis of xanthine oxidase (XO) activity. The analysis was performed using a modification of the procedure of Xia and Zweier (Xia, Y. and J. L. Zweier. 1995, *J. Biol. Chem.* 270:18797–18803). Frozen tissue samples were ground and homogenized in a potassium phosphate buffer, pH 7.8, containing I mM phenylmethylsulfonylfluoride (PMSF) and 10 mM dithiothreitol (DTT), which prevented the in vitro conversion of xanthine dehydrogenase to xanthine oxidase. After repeated centrifugation (600 g ×20 min at 4° C., and 105,000 g×60 min at 4° C.), the lipid layer was removed, and the supernatants passed through a Sephadex G-25 column (Pharmacia Biotech Inc.) equilibrated with the phosphate buffer. The processed effluent was then assayed spectrophotometrically (Beckman DU640 spectrophotometer) at 295 nm for the production of uric acid in the presence of 0.15 mM xanthine. The reaction mixture contained 0.1 mL of effluent, in 50 mM phosphate buffer containing PMSF and DTT, and 0.15 mM xanthine in a 1 mL cuvette at room temperature. Analyses were performed in pairs in the absence and presence of allopurinol to block XO.

Figure 10:
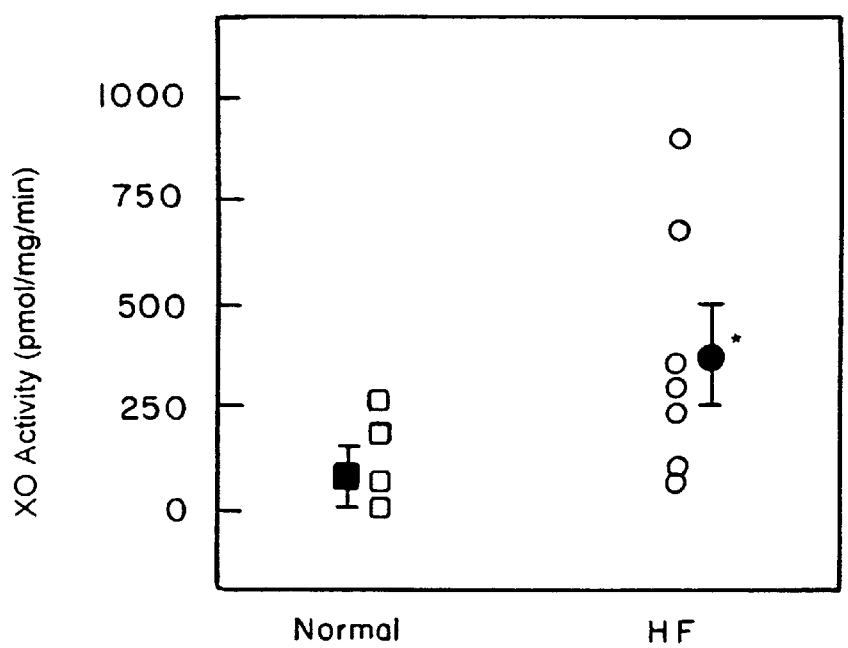
FIG. 10 shows graphically the results of Example 6 which follows, specifically the comparison of xanthine oxidase activity in normal and heart failure dogs.

The activity of xanthine oxidase in failing hearts was compared to normal controls. Results from experiments are shown in FIG. 10. These results indicate that XO activity was significantly increased in failing hearts compared to normal controls. This increase of XO activity during heart failure may be responsible for the increased effects of allopurinol on left ventricular performance and mechanical efficiency observed during heart failure.

This invention has been described in detail with reference to preferred embodiments thereof. However, it will be appreciated that those skilled in the art, upon consideration of this disclosure, may make modifications and improvements within the spirit and scope of the invention.

What is claimed is:

1. A method for treating heart failure in a mammal suffering from or susceptible to heart failure, comprising selecting a mammal for treatment of heart failure that is suffering from or susceptible to heart failure and administering to the selected mammal a therapeutically effective amount of a compound that provides increased cardiac contractile force as measured in a standard in vitro calcium-sensitizing assay.

2. A method for enhancing efficiency of cardiac contraction in a mammal, comprising selecting a mammal in need of enhanced efficiency of cardiac contraction and administering to the selected mammal an effective amount of a xanthine oxidase inhibitor compound.

3. The method of claim 1 or claim 2 wherein the compound is administered to the mammal within about 6 hours after the mammal has suffered heart failure.

4. The method of claim 1 or claim 2 wherein the compound is administered to the mammal within about 18 hours after the mammal has suffered heart failure.

5. The method of claim 1 or claim 2 wherein the compound is administered to the mammal for at least about 1 week after the mammal has suffered heart failure.

6. The method of claim 1 or claim 2 wherein the compound is administered to the mammal for at least about 4 weeks after the mammal has suffered heart failure.

7. The method of claim 1 or claim 2 wherein the mammal is suffering from or susceptible to congestive heart failure.

8. The method of claim 1 or claim 2 wherein the mammal is suffering from or susceptible to cardiogenic shock.

9. A method for treatment of a disorder of cardiac contractility in a mammal suffering from or susceptible to the disorder, comprising selecting a mammal suffering from or susceptible to a disorder of cardiac contractility and administering to the selected mammal a therapeutically effective amount of a xanthine oxidase inhibitor compound.

10. A method for treating heart failure in a mammal suffering from or susceptible to heart failure, comprising selecting a mammal that is suffering from or susceptible to heart failure and administering to the selected mammal a therapeutically effective amount of a xanthine oxidase inhibitor compound.

11. The method of claim 10 wherein the compound is administered to the mammal within about 6 hours after the mammal has suffered heart failure.

12. The method of claim 10 wherein the compound is administered to the mammal within about 18 hours after the mammal has suffered heart failure.

13. The method of claim 10 wherein the compound is administered to the mammal for at least about 1 week after the mammal has suffered heart failure.

14. The method of claim 10 wherein the compound is administered to the mammal for at least about 4 weeks after the mammal has suffered heart failure.

15. The method of claim 10 wherein the mammal is suffering from or susceptible to congestive heart failure.

16. The method of claim 10 wherein the mammal is suffering from or susceptible to cardiogenic shock.

17. A method for treatment method for a disorder of cardiac contractility in a mammal suffering from or susceptible to the disorder, comprising administering to the mammal a therapeutically effective amount of a compound that inhibits xanthine oxidase.

18. The method of claim 17 wherein a mammal suffering from a disorder of cardiac contractility is selected for treatment for the disorder, and the compound is then administered to the selected mammal.

19. The method of claim 17 wherein the disorder of cardiac contractility is heart failure.

20. The method of claim 17 wherein the disorder of cardiac contractility is congestive heart failure.

21. The method of claim 17 wherein the disorder of cardiac contractility is cardiogenic shock.

22. A method of claim 1, 2, 9, 10 or 17 wherein the compound induces at least about a 10 percent increase in cardiac contractile force in a standard in vitro calcium-sensitizing assay.

23. A method of claim 1, 2, 9, 10 or 17 wherein the compound induces at least about a 20 percent increase in cardiac contractile force in a standard in vitro calcium-sensitizing assay.

24. A method of claim 1, 2, 9, 10 or 17 wherein the compound induces at least about a 3 percent decrease in intracellular calcium concentration as measured in a standard in vitro calcium-sensitizing assay.

25. A method of claim 1, 2, 9, 10 or 17 wherein the compound induces at least about a 5 percent decrease in intracellular calcium concentration as measured in a standard in vitro calcium-sensitizing assay.

26. The method of any one of claims 1, 2, 9, 10 or 17 wherein the compound is administered to a human.

27. A method of claim 1, 2, 9, 10, or 17 wherein the administered compound is allopurinol or a pharmaceutically acceptable salt thereof.

28. A method of claim 1, 2, 9, 10 or 17 wherein the administered compound is oxypurinol or a pharmaceutically acceptable salt thereof.

29. A method of claim 1, 2, 9, 10 or 17 wherein the compound corresponds to the following Formula I

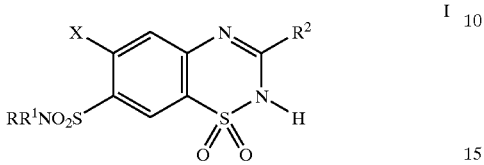

wherein R, $R^1$ and $R^4$ are similar or dissimilar groups selected from hydrogen and lower alkyl having from 1 to about 5 carbon atoms, X is selected from halogen, trifluoromethyl, and lower alkyl, and $R^2$ is a diazine attached through one of its carbon atoms to the benzothiadiazine nucleus.

30. A method of claim 1, 2, 9, 10 or 17 wherein the compound corresponds to the following Formulae II:

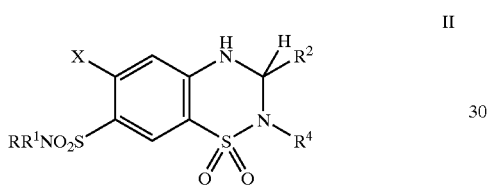

wherein R, $R^1$ and $R^4$ are similar or dissimilar groups selected from hydrogen and lower alkyl having from 1 to about 5 carbon atoms, X is selected from halogen, trifluoromethyl, and lower alkyl, and $R^2$ is a diazine attached through one of its carbon atoms to the benzothiadiazine nucleus.

31. A method of claim 1, 2, 9, 10 or 17 wherein the compound corresponds to the following Formulae III:

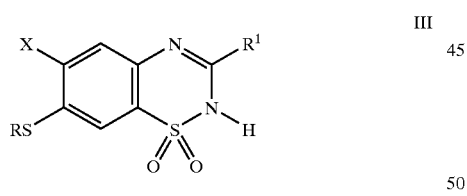

wherein X represents halo, $C_{1-3}$-alkyl or trifluoromethyl; R represents hydrogen, a straight or branched chain lower alkyl having from 1 to 6 carbon atoms and phenyl-lower alkyl having from 1 to 3 carbon atoms; $R^1$ represents hydrogen, lower alkyl having from 1 to 5 carbon atoms or substituted lower alkyl wherein the substituent is mono or dihalo, and phenyl, the group —$CO_2$ lower alkyl having from 1 to 5 carbon atoms, an azine optionally substituted with one or more lower alkyl having 1 to 3 carbon atoms or a diazine optionally substituted with one or more lower alkyl having from 1 to 3 carbon atoms, or the group —$CONR^2R^3$ wherein $R^2$ and $R^3$ can be similar or dissimilar and selected from hydrogen, lower alkyl having 1 to 5 carbon atoms or hydroxy substituted lower alkyl having 1 to 5 carbon atoms.

32. A method of claim 1, 2, 9, 10 or 17 wherein the compound corresponds to the following Formulae IV:

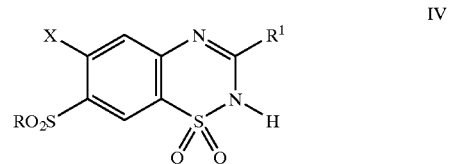

wherein X represents halo, $C_{1-3}$-alkyl and trifluoromethyl; R represents a straight or branched chain lower alkyl having from 1 to 6 carbon atoms and phenyl-lower alkyl having from 1 to 3 carbon atoms; $R^1$ represents (1) hydrogen, (2) lower alkyl having from 1 to 5 carbon atoms or substituted lower alkyl wherein the substituent is mono, di- or trihalo, and phenyl, (3) the group —$CO_2R^2$ wherein R-2- is hydrogen or lower alkyl having from 1 to 5 carbon atoms, (4). the group —$CONH_2$ or (5) an azine optionally substituted with one or more lower alkyl having 1 to 3 carbon atoms or a diazine optionally substituted with one or more lower alkyl having from 1 to 3 carbon atoms.

33. A method of claim 1, 2, 9, 10 or 17 wherein the compound corresponds to the following Formulae V:

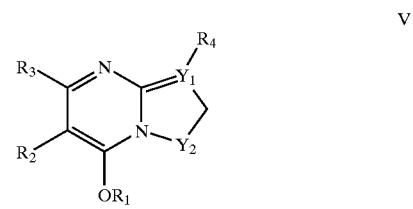

wherein $Y_1$ and $Y_2$ are carbon or nitrogen; $R_1$ is H or an alkali metal or ammonium; $R_2$ is H, $CH_3$, a halogen, phenylazo or $NO_2$; $R_3$ is $OR_1$, H, or a halogen; and $R_4$ is H, $NO_2$ or a halogen.

34. A method of claim 1, 2, 9, 10 or 17 wherein the compound corresponds to the following Formulae VI:

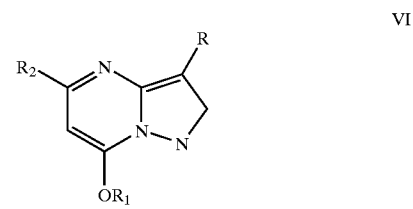

wherein R is an aromatic or substituted aromatic nucleus, $R_1$ is H, an alkali metal or ammonium, and $R_2$ is H or $OR_1$.

35. A method of claim 1, 2, 9, 10 or 17 wherein the compound corresponds to the following Formulae VII:

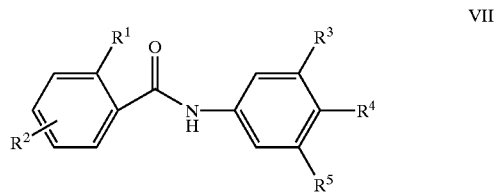

wherein $R^1$ is —OH or

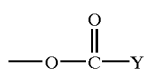

in which Y is lower alkyl or phenyl; $R^2$ is substituted either at the 4'-position or at the 5'-position and is hydrogen, fluoro, bromo, chloro, hydroxy, lower alkyl or

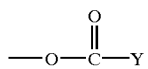

in which Y is lower alkyl or phenyl; $R^3$ is chloro, bromo or lower alkyl; $R^4$ is hydroxy, amine, lower alkoxy or

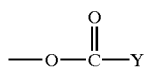

in which Y is lower alkyl or phenyl; $R^5$ is hydrogen, fluoro, bromo, chloro, carboxyl, lower alkyl or

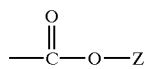

in which Z is lower alkyl; and the nontoxic, pharmaceutically acceptable metal salts of said compound in which $R^5$ is carboxyl.

36. A method of claim 1, 2, 9, 10 or 17 wherein the compound corresponds to the following Formulae VIII:

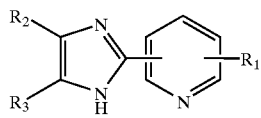

wherein $R_1$ is hydrogen or alkyl containing 1 to 3 carbon atoms; $R_2$ is halogen; and $R_3$ is halogen or —$CF_3$; or a pharmaceutically acceptable salt thereof.

37. A method of claim 1, 2, 9, 10 or 17 wherein the compound corresponds to the following Formulae IX:

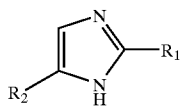

wherein $R_1$ is selected from the group consisting of monohalo-phenyl, dihalo-phenyl and pyridyl, halo is Cl, Br, I or F, $R_2$ is selected from the group consisting of $C_1$–$C_5$ alkyl-S—, $C_1$–$C_5$ alkyl-SO—, $C_1$–$C_5$ alkyl-$SO_2$— and $R_3R_4N$—$SO_2$—, and $R_3$ and $R_4$ are independently selected from H, $C_1$–$C_5$ alkyl and hydroxy substituted $C_2$–$C_5$ alkyl.

38. A method of claim 1, 2, 9, 10 or 17 wherein the compound corresponds to the following Formulae X:

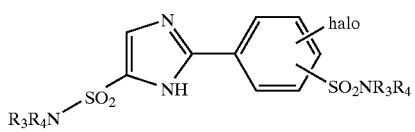

wherein $R_1$ is selected from the group consisting of monohalo-phenyl, dihalo-phenyl and pyridyl, halo is Cl, Br, I or F; $R_2$ is selected from the group consisting of $C_1$–$C_5$ alkyl-S—, $C_1$–$C_5$ alkyl-SO—, $C_1$–$C_5$ alkyl-$SO_2$— and $R_3R_4N$—$SO_2$—, and $R_3$ and $R_4$ are independently selected from H, $C_1$–$C_5$ alkyl and hydroxy substituted $C_2$–$C_5$ alkyl.

39. A method of claim 1, 2, 9, 10 or 17 wherein the compound corresponds to the following Formulae XI:

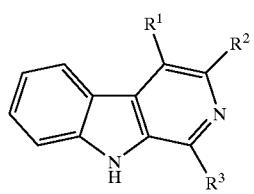

wherein one of $R^1$ and $R^2$ is hydrogen and the other is hydrogen, hydroxy or —$OR^4$ wherein $R^4$ is alkanoyl of 2 to 7 carbon atoms, tosyl or mesyl and $R^3$ is hydroxymethyl, formyl, carboxy or carbalkoxy wherein alkoxy contains 1 to 6 carbon atoms.

40. A method of claim 1, 2, 9, 10 or 17 wherein the compound corresponds to the following Formulae XII:

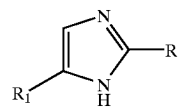

wherein R is 3-pyridyl or 4-pyridyl and $R_1$ is $C_1$–$C_5$ alkyl.

41. A method of claim 1, 2, 9, 10 or 17 wherein the compound corresponds to the following Formulae XIII:

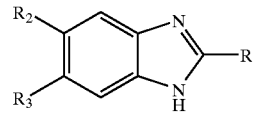

wherein R is 3-pyridyl or 4-pyridyl, $R_2$ is bromo or chloro, and $R_3$ is hydrogen, bromo or chloro.

42. A method of claim 1, 2, 9, 10 or 17 wherein the compound corresponds to the following Formulae XIV:

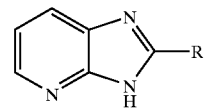

wherein R is 3-pyridyl or 4-pyridyl.

43. A method of claim 1, 2, 9, 10 or 17 wherein the compound corresponds to the following Formulae XV:

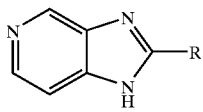

XV wherein R is 3-pyridyl or 4-pyridyl.

44. A method of claim 1, 2, 9, 10 to 17 wherein the compound corresponds to the following Formulae XVI:

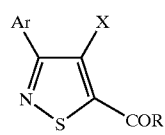

XVI wherein Ar is pyridyl, thienyl, phenyl or

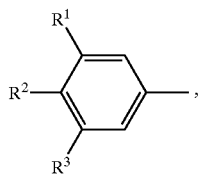

wherein $R^1$, $R^2$ and $R^3$ are individually H, $CF_3$, halogen, alkyl or O-alkyl or $R^1$ and $R^2$ or $R^2$ and $R^3$ when taken together are methylenedioxy; X is $NH_2$, H, halogen, OH or NH-alkyl; R is OH, OM, O-alkyl, $NH_2$, NH-alkyl or N(alkyl)$_2$; wherein halogen is Cl, F, I, or Br; and M is a nontoxic cation.

45. A method of claim 1, 2, 9, 10 or 17 wherein the compound corresponds to the following Formulae XVII:

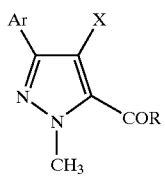

XVII wherein Ar is pyridyl, thienyl or

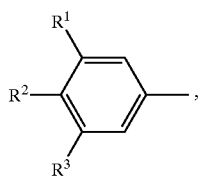

wherein $R^1$, $R^2$ and $R^3$ are individually H, $C_{1-3}$ haloalkyl, F, Br, Cl, I, $C_{1-3}$ alkyloxy, $R^1$ and $R^2$ or $R^2$ and $R^3$ taken together represent methylmedioxy, provided at least one of $R^1$, $R^2$ and $R^3$ is H, one of $R^1$, $R^2$ and $R^3$ is other than H and only one of $R^1$, $R^2$ and $R^3$ can be I; R is OH, OM, $NH_2$, N-alkyl, N(alkyl)$_2$, O-alkyl or N-alkenyl-N(alkyl)$_2$; X is $NH_2$, OH, H, F, Cl, Br, I or $C_{1-3}$ alkyl; alkyl is $C_{1-5}$ alkyl; alkenyl is $(CH_2)_2$ or $(CH_2)_3$; and M is a nontoxic cation.

46. A method of claim 1, 2, 9, 10 or 17 wherein the compound corresponds to the following Formulae XVIII:

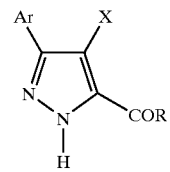

XVIII wherein Ar is pyridyl, thienyl or

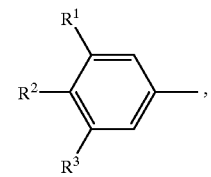

wherein $R^1$, $R^2$ and $R^3$ are individually H, $C_{1-3}$ haloalkyl, F, Br, Cl, I, $C_{1-3}$ alkyloxy, $R^1$ and $R^2$ or $R^2$ and $R^3$ taken together represent methylmedioxy, provided at least one of $R^1$, $R^2$ and $R^3$ is H, one of $R^1$, $R^2$ and $R^3$ is other than H and only one of $R^1$, $R^2$ and $R^3$ can be I; R is OH, OM, $NH_2$, N-alkyl, N(alkyl)$_2$, O-alkyl or N-alkenyl-N(alkyl)$_2$; X is $NH_2$, OH, H, F, Cl, Br, I or $C_{1-3}$ alkyl; alkyl is $C_{1-5}$ alkyl; alkenyl is $(CH_2)_2$ or $(CH_2)_3$; and M is a nontoxic cation.

47. A method of claim 1, 2, 9, 10 or 17 wherein the compound corresponds to the following Formulae XIX:

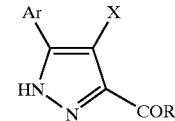

XIX wherein Ar is pyridyl, thienyl or

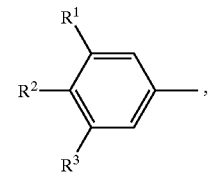

wherein $R^1$, $R^2$ and $R^3$ are individually H, $C_{1-3}$ haloalkyl, F, Br, Cl, I, $C_{1-3}$ alkyloxy, $R^1$ and $R^2$ or $R^2$ and $R^3$ taken together represent methylmedioxy, provided at least one of $R^1$, $R^2$ and $R^3$ is H, one of $R^1$, $R^2$ and $R^3$ is other than H and only one of $R^1$, $R^2$ and $R^3$ can be I; R is OH, OM, $NH_2$, N-alkyl, N(alkyl)$_2$, O-alkyl or N-alkenyl-N(alkyl)$_2$; X is $NH_2$, OH, H, F, Cl, Br, I or $C_{1-3}$ alkyl; alkyl is $C_{1-5}$ alkyl; alkenyl is $(CH_2)_2$ or $(CH_2)_3$; and M is a nontoxic cation.

48. A method of claim 1, 2, 9, 10 or 17 wherein the compound corresponds to the following Formulae XX:

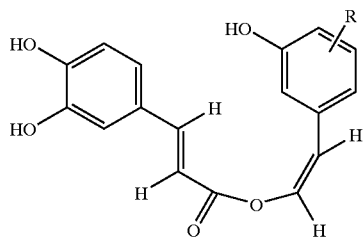

XX wherein R is 4'-OH or 5'-OH.

49. A method of claim 1, 2, 9, 10 or 17 wherein the compound corresponds to the following Formulae XXI:

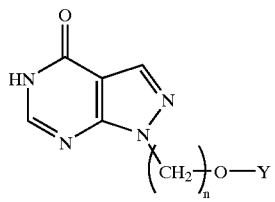

XXI wherein n is an integer between 2 and 6, Y is H or CO—A, wherein A is a racemic or chiral amino acid, dipeptide, tripeptide, tetrapeptide, or pentapeptide.

50. A method of claim 1, 2, 9, 10 or 17 wherein the compound corresponds to the following Formulae XXII:

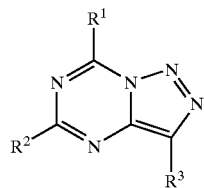

XXII wherein $R^1$ is hydroxy or a lower alkanoyloxy, $R^2$ is hydrogen atom, hydroxy, or mercapto, $R^3$ is an unsaturated heterocyclic group containing nitrogen or sulfur atom as the hetero atom; naphthyl; or a phenyl.

51. A method of claim 1, 2, 9, 10 or 17 wherein the compound corresponds to the following Formulae XXIII:

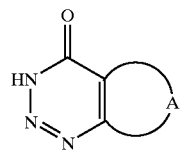

XXIII wherein A is a grouping of the formula

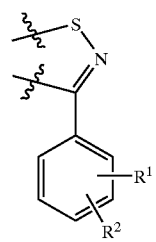

(a)

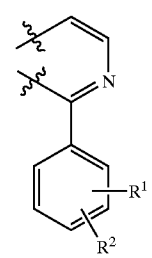

(b)

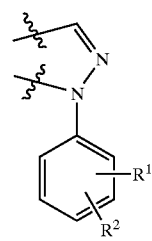

(c)

in which $R^1$ and $R^2$ each individually is hydrogen, halogen, trifluoromethyl, nitro, amino, cyano, $C_1$–$C_6$-alkyl, $C_1$–$C_6$-alkoxy, $C_3$–$C_6$-alkenyloxy, $C_1$–$C_6$-alkylthio, $C_1$–$C_6$-alkanoylamino, aryloxy, aryl-($C_1$–$C_6$-alkyl), aryl-($C_1$–$C_6$-alkoxy), aryl-($C_1$–$C_6$-alkoxy) carbonylamino or —O—$CH_2$—$R^3$, or $R^1$ and $R^2$ on adjacent carbon atoms together are —CH=CH—CH=CH— or —$CH_2$—$CH_2$—O—, and $R^3$ is hydroxy-($C_1$–$C_4$-alkyl) or vicinal dihydroxy-($C_2$–C5-alkyl).

52. A method for treating heart failure in a mammal suffering from or that has suffered heart failure, comprising selecting a mammal for heart failure treatment that is suffering from or has suffered heart failure and administering to the selected mammal a therapeutically effective amount of allopurinol or a pharmaceutically acceptable salt thereof.

53. The method of claim 52 wherein the mammal has suffered congestive heart failure.

54. The method of claim 52 wherein the mammal has suffered from cardiogenic shock.

55. The method of any one of claim 52 through 54 wherein the allopurinol is administered regularly to the mammal for at least two weeks.

56. The method of any one of claims 52 through 54 wherein the allopurinol is administered regularly to the mammal for at least four weeks.

57. The method of any one of claim 52 through 54 wherein the allopurinol is administered to the mammal within about 24 hours after having suffered heart failure.

58. The method of any one of claim 52 through 54 wherein the mammal is a human.

59. A method for treating heart failure in a mammal suffering from or has suffered heart failure comprising selecting a mammal for heart treatment that is suffering from or susceptible to heart failure and administering to the selected mammal a therapeutically effective amount of oxypurinol or a pharmaceutically acceptable salt thereof.

60. The method of claim 59 wherein the mammal has suffered congestive heart failure.

61. The method of claim 59 wherein the mammal has suffered from cardiogenic shock.

62. The method of any one of claims 59 through 61 wherein the oxypurinol is administered regularly to the mammal for at least two weeks.

63. The method of any one of claim 59 through 61 wherein the oxypurinol is administered regularly to the mammal for at least four weeks.

64. The method of any one of claim 59 through 61 wherein the oxypurinol is administered to the mammal within about 24 hours after having suffered heart failure.

65. The method of any one of claim 59 through 61 wherein the mammal is a human.

* * * * *